(12) United States Patent
Noda et al.

(10) Patent No.: US 6,933,422 B2
(45) Date of Patent: Aug. 23, 2005

(54) $Na_v2$ CHANNEL GENE-DEFICIENT MICE

(75) Inventors: Masaharu Noda, Okazaki (JP); Eiji Watanabe, Okazaki (JP)

(73) Assignee: Japan as represented by Director of General of Okazaki National Research Institute, Okazaki (JP)

(*) Notice: Subject to any disclaimer, the term of this patent is extended or adjusted under 35 U.S.C. 154(b) by 128 days.

(21) Appl. No.: 09/920,653

(22) Filed: Aug. 3, 2001

(65) Prior Publication Data

US 2002/0104113 A1 Aug. 1, 2002

(30) Foreign Application Priority Data

| Aug. 4, 2000 | (JP) | 2000-237320 |
|---|---|---|
| Aug. 9, 2000 | (JP) | 2000-241637 |
| Jul. 23, 2001 | (JP) | 2001-222263 |

(51) Int. Cl.$^7$ .................. A01K 67/027; A01K 67/00; A01K 67/033; G01N 33/00; C12N 15/00; C12N 15/09; C12N 15/63; C12N 15/70; C12N 15/74; C12N 15/85; C12N 15/87; C12N 15/02

(52) U.S. Cl. .................. 800/18; 800/3; 800/8; 800/13; 800/21; 800/22; 435/455; 435/463; 435/320.1; 435/325

(58) Field of Search .................. 800/3, 8, 13, 18, 800/21, 22, 25; 435/455, 463, 320.1, 325

(56) References Cited

U.S. PATENT DOCUMENTS 4,946,778 A 8/1990 Ladner

OTHER PUBLICATIONS

Moreadith, R.W. et al. Gene Targeting in Embryonic Stem Cells: The New Physiology and Metabolism. J. Mol. Med, 1997, 75:208–216.*
Sanford et al. Meth in Mol. Bio, 158:217–225, 2001.*
Mullins et al. Journal of Clinical Investigation, 1996.*
Pera et al. Journal of Cell Science 113: 5–10 (2000).*
Encyclopedia Britannica, http://www.search.eb.com/dictionary.*
Noda et al, "Existence of Distinct Sodium Channel Messenger RNAs in Rat Brain", Nature, vol. 320:188–192, (1986).
Kayano et al., "Primary Structure Of Rat Brain Sodium Channel III Deduced From The cDNA Sequence", Federation of European Biochemical Societies, vol. 228(1):187–194, (1988).
Sontheimer et al., "Voltage–Gated Na+ Channels In Glia: Properties And Possible Functions", TINS, Elsevier Science Ltd., vol. 19(8):325–331, (1996).
Reese et al., "Immunocytochemical Localization of NaCh6 In Cultured Spinal Cord Astrocytes", GLIA, Wiley–Liss, Inc., vol. 26:92–96, (1999).
Gautron et al., "The glial Voltage–Gated Sodium Channel: Cell– And Tissue–Specific MRNA Expression", Proc. Natl. Acad. Sci., USA, Neurobiology, vol. 89:7272–7276, (1992).
George, Jr. et al., "Molecular Cloning Of An Atypical Voltage–Gated Socium Channel Expressed In Human Heart And Uterus: Evidence For A Distinct Gene Family", Proc. Natl. Acad. Sci, USA, Physiology, vol. 89:4893–4897, (1992).
Felts et al., "NaG: A Sodium Channel–Like mRNA Shared By Schwann Cells And Other Natural Crest Derivatives", GLIA, Wiley–Liss, Inc., vol. 21:269–276, (1997).
Felts et al., "Sodium Channel a–Subunit mRNAs I, II, III, NaG, Na6 And hNE (Pn1): Different Expression Patterns In Developing Rat Nervous System", Molecular Brain Research, Elsevier Science B.V., vol. 45:71–82, (1997).
"Continuous Cultures Of Fused Cells Secreting Antibody Of Predefined Specificity", Nature, vol. 256:495–497, (1975).
Kozbor et al., "The Production Of Monoclonal Antibodies From Human Lymphocytes", Immunology Today, Elsevier Biomedical Press, vol. 4(3):72–79, (1983).
Cole et al., "The EBV–Hybridoma Technique And Its Application To Human Lung Cancer", Monoclonal Antibodies And Cancer Therapy, Department of Microbiology & Immunology Queen's University, Alan R. Liss, Inc., pp. 77–96, (1985).
Pietri–Rouxel et al., "The Biochemical Effect Of The Naturally Occuring Trp64→Arg Mutation On Human β3–Adrenoceptor Activity", Eur. J. Biochem., FEBS, vol. 247:1174–1179, (1997).

(Continued)

Primary Examiner—Joe Waitach
Assistant Examiner—Thaian N. Ton
(74) Attorney, Agent, or Firm—Venable LLP; Robert Kinberg; Ann S. Hobbs

(57) ABSTRACT

An object of the present invention is to provide a null mutant non-human animal showing salt intake behavior similar to that of wild-type animals under water-sufficient conditions and showing much more intakes of hypertonic saline compared with wild-type animals under water- and salt-depleted conditions, for example, an $Na_v2$ gene-deficient non-human animal, which is useful as a model animal of excessive salt intake experiments.

The object will be attained by following process: mouse genomic libraries are screened with rat NaG cDNA as a probe, then $Na_v2$ gene of genomic DNA is isolated, and a targeting vector is constructed by inserting marker gene such as neo gene into the exon of $Na_v2$. After thus constructed targeting vector is induced to ES cells, homologously recombined ES cells are selected, then germ line chimeric mice are constructed with this ES cells strain, and they are hybridized with the wild-type mice and heterozygous mutant mice are obtained. By intercrossing of thus obtained heterozygous mutant mice, $Na_v2$ knockout mice are constructed.

2 Claims, 11 Drawing Sheets

(4 of 11 Drawing Sheet(s) Filed in Color)

OTHER PUBLICATIONS

Yagi, et al., "A Novel Negative Selection For Homologous Recombinants Using Diphtheria Toxin A Fragment Gene", Analytical Biochemistry, Academic Press, Inc., vol. 214:77–86, (1993).

Shintani et al., "Neurons As Well As Astrocytes Express Proteoglycan–Type Protein Tyrosine Phosphatase ζ/RPTPβ: Analysis of Mice In Which The PTPζ/RPTPβ Gene Was Replaced With The LacZ Gene", Neuroscience Letters, Elsevier Science Ireland Ltd., vol. 247:135–138, (1998).

Knittle et al., "Immunolocalization Of The Mnav2.3 Na+ Channel In Mouse Heart: Upregulation In Myometrium During Pregnancy", The American Physiological Society, pp. C688–C696, (1996).

CH. Pilgrim, "Transport Function Of Hypothalamic Tanycyt Ependyma: How Good Is The Evidence", Neuroscience, vol. 3:277–283, (1978).

Hatton, "Pituicytes, Glia And Control Of Terminal Secretion", J. exp. Biol., vol. 139:67–79, (1988).

Bourque et al., "Osmoreceptors In The Central Nervous System", Annu. Rev. Physiol., vol. 59:601–619, (1997).

Fitzsimons, "Angiotensin, Thirst, And Sodium Appetite", Physiological Reviews, vol. 78(3):583–686, (1998).

Andersson, "Regulation of Water Intake", Physiological Reviews, vol. 58(3):582–603, (1978).

Johnson et al., "The Extended Amygdala And Salt Appetite", Annals New York Academy of Sciences, vol. 877:258–280, (1999).

Davis et al., Basic Methods in Molecular biology, (1986).

Joseph Sambrook et al.. *Molecular Cloning: A Laboratory Manual, 1989*, 3rd Ed., vols. 1–3, Cold Spring Harbor Laboratory Press, Cold Spring Harbor, N.Y.

M. Renganathan et al. "α–SNS Produces, the Slow TTX–Resistant Sodium Current in Large Cutaneous Afferent DRG Neurons". *J. Neurophysiol*, 2000, pp. 710–718, vol. 84.

Mirek Jurzak et al., "Primary Culture Of Circumventricular Organs From the Rat Brain Lamina Terminals", *Brain Research*, 1994, vol. 662, pp. 198–208.

Alan Kim Johnson, "Sensory Circumventricular Organs and Brain Homeostatic Pathways", Federation of American Societies for Experimental Biology, vol. 7, No. 8, 1993, pp. 678–686.

Antonio Felipe et al., "Primary Structure and Differential Expression During Development and Pregnancy of a Novel Voltage–gated Sodium Channel in the Mouse", Journal of Biological Chemistry, vol. 269, No. 48, 1994, pp. 30125–30131.

A. N. Akopian et al, "Structure and Distributiono f a Broadly Espressed Atypical Sodium Channel", Febs Letters, Elsevier Science Publishers, Amsterdam, NL, vol. 400, No. 2, Jan. 3, 1997, pp. 183–187.

Stephen J. Quinn et al, "Sodium and Ionic Strenght Sensing by the Calcium Receptor", Journal of Biological Chemistry, vol. 273, No. 31, Jul. 31, 1998, pp. 19579–19586.

Eiji Watanabe et al., "Nav2/NaG Channel is Involved in Control of Salt–intake Behavior in the CNS", Journal of Neuroscience, vol. 20, No. 20, Oct. 15, 2000, pp. 7743–7751.

* cited by examiner

□ Before
■ After 24-h water deprivation

$NA_V2$ CHANNEL GENE-DEFICIENT MICE

TECHNICAL FIELD TO WHICH THE INVENTION PERTAINS

This invention relates to a non-human animal whose function of $Na_v2$ channel gene is deficient on its chromosome that shows salt intake behavior similar to that of wild-type animals under water-sufficient conditions and shows much more intakes of hypertonic saline compared with wild-type animals under water- and salt-depleted conditions, a protein acting as a sensor of extracellular sodium ion level, a gene that codes for said protein, and the like.

PRIOR ART

Voltage-dependent sodium channels as well as voltage-dependent potassium channels are known as the ion channels which play the main role in the generation and the propagation of action potential in excitable cells such as nerve cells, muscle cells, and the like. A sodium channel molecule comprises an ion-selective channel with voltage-sensors, and is consisted of α-subunits comprised of glycoprotein of 270 kDa, and 1 or 2 smaller β-subunits. Voltage-dependent sodium channels are closed when the cell membrane is in resting potential (normally −70 to −90 mV), but they open when the cell membrane depolarizes and close approximately 1 msec later. Therefore, it is said that a sodium channel protein molecule has a voltage-sensor that senses the membrane potential, and opens the channel, a selective filter for filtering a sodium ion selectively, and inactivation gate.

Since the identification of a sodium channel protein α-subunit cDNA type I, II, and III in the brain (Nature 320, 188–192(1986), FEBS Lett. 228, 187–194(1988)) by the inventors of the present invention, multiple structurally related isoforms of the α-subunit have been cloned from various tissues, forming a multigene family. In addition to the excitable cells, it has recently been found that glial cells also express voltage-sensitive sodium currents (Trends Neurosci. 19, 325–332(1996)). In situ hybridization, RT-PCR, Northern blot analysis and immunocytochemistry have clearly demonstrated the presence of brain-type I, II, III, H1, $Na_s$, NaCH6 and the like in glial cells (Glia 26, 92–96 (1999)). However, the functional roles of these voltage-dependent sodium channels in so-called electrically inexcitable cells have not yet been delineated.

Several years ago, a partial cDNA homologous to the voltage-dependent sodium channel α-subunit was cloned from a cDNA library derived from rat astrocytes, and designated NaG (Proc. Natl. Acad. Sci. USA 89, 7272–7276 (1992)). Subsequently, similar α-subunit isoforms were independently cloned from various animal species: $Na_v2.1$ from human heart (Proc. Natl. Acad. Sci. USA 89, 4893–4897(1992)), $Na_v2.3$ from a mouse arterial tumor cell line (J. Biol. Chem. 269, 30125–30131), and SCL11 from rat dorsal root ganglia which corresponds to splicing variant of NaG (FEBS Lett. 400, 183–187(1997)). From the sequence homology, it is possible to assume that they are species orthologues and to classify them into another subfamily of α-subunit of voltage-dependent sodium channels (NaCh), namely, subfamily 2 NaCh ($Na_v2$). Their overall amino acid sequences had less than 50% identity with those of the previously cloned voltage-dependent sodium channels, and the sequences are characterized as rather unique even in the regions associated with ion selectivity and voltage-dependent activation and inactivation. Such regions are perfectly conserved in all other subfamily members, suggesting that the $Na_v2$ has specific channel properties. However, all the attempts to express functional $Na_v2$ channels in heterologous expression systems using such as Xenopus oocytes, CHO cells, HEK293 cells and the like have been unsuccessful, and the function of $Na_v2$ channels in vivo has been totally unknown.

NaG/SCL11 was originally thought to be one of the voltage-dependent sodium channels (NaChs) expressed in astrocytes because it was cloned from astrocytes, but subsequent in situ hybridization studies revealed that $Na_v2$ is expressed not in astrocytes but in Schwann cells and the spinal sensory neurons in vivo (Glia 21, 269–276(1997)). Relatively high levels of NaG mRNA are detected outside of the nervous system, particularly in lung and heart. In addition, RNase protection and Northern blot analyses demonstrated the presence of NaG mRNA in the central nervous system. However, it has been reported that NaG mRNA was not detectable by in situ hybridization using a non-isotopic probe except in the mesencephalic nucleus V. (Mol. Brain Res. 45, 71–82(1997)), suggesting that NaG mRNA is broadly expressed at a low level throughout the central nervous system or expressed restrictedly in specific regions in the central nervous system. The distribution of the NaG channel among these diverse tissues and cell-types including electrically inexcitable cells, suggests a role for this channel other than in action-potential generation and propagation.

An Object to be Attained by the Invention

So far, a model animal for excessive salt intake experiments showing salt intake behavior similar to that of wild-types under water-sufficient conditions and showing abnormal intakes of hypertonic saline compared with wild-types under water- and salt-depleted conditions has not been known. A protein acting as a sensor of extracellular sodium ion level, and a gene that codes for such protein have not been known as well. The object of the present invention is to provide a null mutant non-human animal showing salt intake behavior similar to that of wild-type animals under water-sufficient conditions and showing much more intakes of hypertonic saline compared with wild-type animals under water- and salt-depleted conditions, for example, an $Na_v2$ gene deficient non-human animal, which is useful as said model animal of excessive salt intake experiments, a protein acting as a sensor of extracellular sodium ion level, and a gene that codes for said protein.

Means to Attain the Object

The inventors have intensely studied the function and the role of $Na_v2$ channel in vivo, which was unknown, and generated $Na_v2$ channel knockout mice, then confirmed that $Na_v2$ channel plays a role to sense and control sodium ion level in body fluids. Subsequently, it has been found that these $Na_v2$ channel knockout mice show salt intake behavior similar to that of wild-types under water-sufficient conditions and show abnormal behavior such as much higher intakes of hypertonic saline compared with wild-types under water- and salt-depleted conditions, and thus the present invention has been completed.

In other words, this invention relates to a null mutant non-human animal characterized in showing salt intake behavior similar to that of wild-type animals under water-sufficient conditions and showing much higher intakes of hypertonic saline compared with wild-type animals under water- and salt-depleted conditions, the null mutant non-human animal characterized in showing salt intake behavior similar to that of wild-type animals under water-sufficient conditions and showing much more intakes of hypertonic saline compared with wild-type animals under water- and salt-depleted conditions, wherein the function of $Na_x2$ gene is deficient on its chromosome, the null mutant non-human animal, wherein the non-human animal is a rodent, and the null mutant non-human animal, wherein the rodent is a mouse.

This invention also relates to a gene that codes for a protein acting as a sensor of extracellular sodium ion level, the gene that codes for a protein acting as a sensor of extracellular sodium ion level, wherein the protein is comprised of the amino acid sequence shown in Seq. ID No. 3, or is comprised of an amino acid sequence where one or a few amino acids are deficient, substituted, or added, in the amino acid sequence shown in Seq. ID No. 3, the gene that codes for a protein acting as a sensor of extracellular sodium ion level, which is comprised of DNA that contains a base sequence shown in Seq. ID No. 2 or its complimentary sequence, and a part or whole of those sequences, and the gene that codes for a protein acting as a sensor of extracellular sodium ion level, which is comprised of DNA being hybridized under stringent conditions with DNA that contains a base sequence shown in Seq. ID No. 2 or its complimentary sequence, and a part of or whole of those sequences.

This invention relates to a protein acting as a sensor of extracellular sodium ion level the protein acting as a sensor of extracellular sodium ion level, which is comprised of amino acid sequence shown in Seq. ID No. 3, the protein acting as a sensor of extracellular sodium ion level, which is comprised of amino acid sequence where one or a few amino acids are deficient, substituted, or added, in amino acid sequence shown in Seq. ID No. 3, a fusion protein created by combining a protein acting a sensor of extracellular sodium ion level and a marker protein and/or a peptide tag, and the fusion protein created by combining a protein acting as a sensor of extracellular sodium ion level and a marker protein and/or a peptide tag, wherein the protein acting as a sensor of extracellular sodium ion level is the protein acting as a sensor of extracellular sodium ion level which is comprised of amino acid sequence shown in Seq. ID No. 3, or the protein acting as a sensor of extracellular sodium ion level which is comprised of amino acid sequence where one or a few amino acids are deficient, substituted, or added, in amino acid seciuence shown in Seq. ID No. 3.

This invention also relates to an antibody which specifically combines with a protein acting as a sensor of extracellular sodium ion level, the antibody which specifically combines with a protein acting as a sensor of extracellular sodium ion level wherein the protein acting as a sensor of extracellular sodium ion level is the protein acting as a sensor of extraccilular sodium ion level which is comprised of amino acid sequence shown in Seq. ID No. 3, or the protein acting as a sensor of extracellular sodium ion level which is comprised of amino acid sequence where one or a few amino acids are deficient, substituted, or added, in amino acid sequence shown in Seq. ID No. 3, and the antibody wherein the antibody is monoclonal.

This invention relates to a host cell which contains an expression system that can express a protein acting as a sensor of extracellular sodium ion level, and the host cell which contains an expression system that can express a protein acting as a sensor of extracellular sodium ion level, wherein the protein acting as a sensor of extracellular sodium ion level is the protein acting as a sensor of extracellular sodium ion level which is comprised of amino acid sequence shown in Seq. ID No. 3, or the protein acting as a sensor of extracellular sodium ion level which is comprised of amino acid sequence where one or a few amino acids are deficient, substituted, or added, in amino acid sequence shown in Seq. ID No. 3.

This invention also relates to a transgenic non-human animal which excessively expresses a protein acting as a sensor of extracellular sodium ion level, the transgenic non-human animal which excessively expresses a protein acting as a sensor of extracellular sodium ion level, wherein the protein acting as a sensor of extracellular sodium ion level is the protein acting as a sensor of extracellular sodium ion level which is comprised of amino acid sequence shown in Seq. ID No. 3, or the protein acting as a sensor of extracellular sodium ion level which is comprised of amino acid sequence where one or a few amino acids are deficient, substituted, or added, in amino acid sequence shown in Seq. ID No. 3, and the transgenic non-human animal wherein the non-human animal is a mouse or rat.

This invention relates to a method of screening a material that promotes or suppresses the function or the expression of a protein acting as a sensor of extracellular sodium ion level characterized in using a cell that expresses a protein acting as a sensor of extracellular sodium ion level, and a subject material, the method of screening a material that promotes or suppresses the function or the expression of a protein acting as a sensor of extracellular sodium ion level characterized in using the non-human animal which excessively expresses a protein acting as a sensor of extracellular sodium ion level, the non-human animal which excessively expresses a protein acting as a sensor of extracellular sodium ion level wherein the protein acting as a sensor of extracellular sodium ion level is the protein acting as a sensor of extracellular sodium ion level which is comprised of amino acid sequence shown in Seq. ID No. 3 or the protein acting as a sensor of extracellular sodium ion level which is comprised of amino acid sequence where one or a few amino acids are deficient, substituted, or added, in amino acid sequence shown in Seq. ID No. 3, and the transgenic non-human animal herein the non-human animal is a mouse or rat, and a subject material.

This invention relates to a material that promotes or suppresses the function or the expression of a protein acting as a sensor of extracellular sodium ion level characterized in being available through any one of the screening methods discussed in the preceding paragraph, a medical compound used for curing patients who need promotion of the function or enhancement of the expression of a protein acting as a sensor of extracellular sodium ion level, and containing the protein acting as a sensor of extracellular sodium ion level, the protein acting as a sensor of extracellular sodium ion level which is comprised of amino acid sequence shown in Seq. ID No. 3, or the protein acting as a sensor of extracellular sodium ion level which is comprised of amino acid sequence where one or a few amino acids are deficient, substituted, or added, in amino acid sequence shown in Seq. ID No. 3, or the material that promotes the function or the expression of a protein acting as a sensor of extracellular sodium ion level characterized in being available through any one of the screening methods discussed above, which is comprised of amino acid sequence shown in Seq. ID No. 3, the protein acting as a sensor of extracellular sodium ion level, which is comprised of amino acid sequence where one or a few amino acids are deficient, substituted, or added, in amino acid sequence shown in Seq. ID No. 3 as its effective components, and a medical compound used for curing patients who need suppression of the function or the expression of a protein acting as a sensor of extracellular sodium ion level, and containing the protein acting as a sensor of extracellular sodium ion level, the protein acting as a sensor of extracellular sodium ion level which is comprised of amino acid sequence shown in Seq. ID No. 3, or the protein acting as a sensor of extracellular sodium ion level which is comprised of amino acid sequence where one or a few amino acids are deficient, substituted, or added, in amino acid sequence shown in Seq. ID No. 3, or the material that suppresses the function or the expression of a protein acting as a sensor of extracellular sodium ion level characterized in being available through any one of the screening methods discussed above.

BRIEF EXPLANATION OF DRAWINGS

The patent or application file contains at least one drawing executed in color. Copies of this patent or patent application publication with color drawing(s) will be provided by the Office upon request and payment of the necessary fee.

MODE FOR CARRYING OUT THE INVENTION

Figure 1:
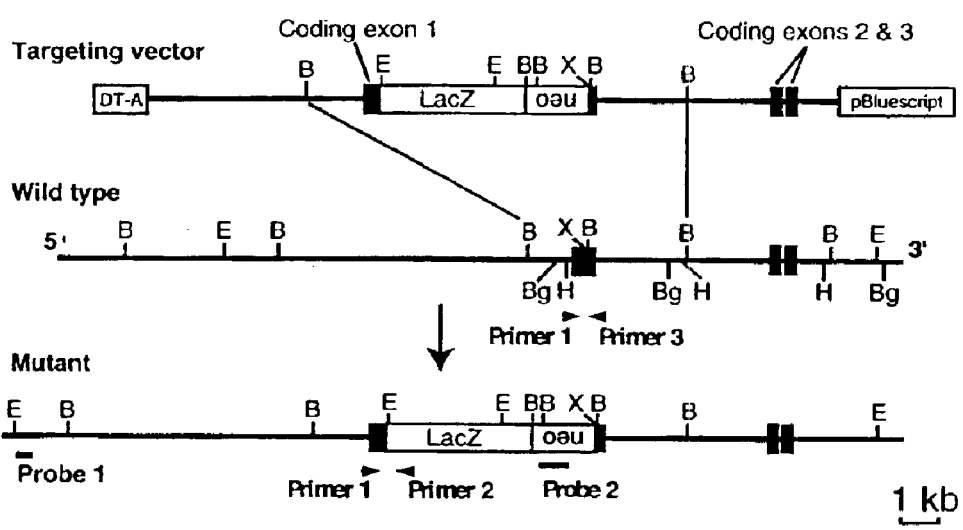
FIG. 1 is a view showing a gene map of $Na_v2$ knockout mice of the present invention (a), the result of Southern blot technique (b), genomic PCR (c) and Western blot technique (d) of genomic DNA.
Figure 1:
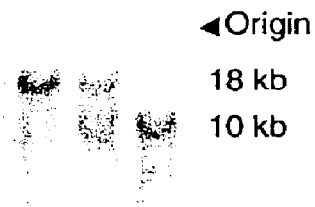
Figure 1:
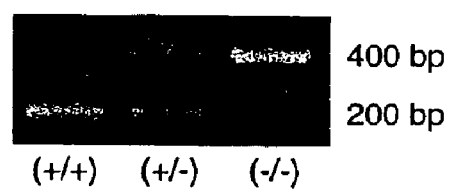
Figure 1:
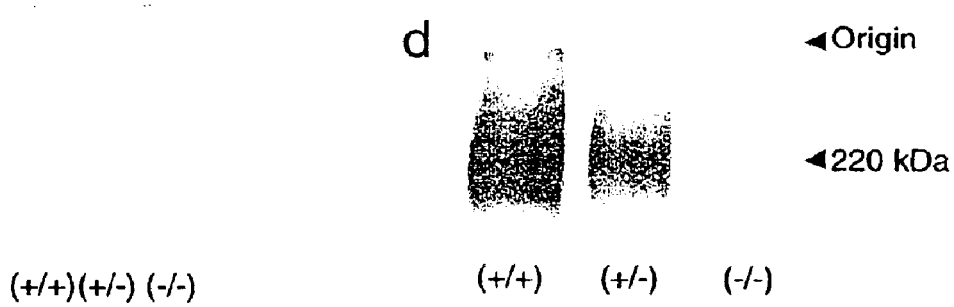

The null mutant non-human animal of the present invention is not particularly limited, any non-human animal showing salt intake behavior similar to wild-types under water-sufficient conditions and showing much more intakes of hypertonic saline compared with wild-types under water- and salt-depleted conditions will suffice, however, the null mutant non-human animal whose function of $Na_v2$ genes is deficient on its chromosome is exemplified as a concrete example of such non-human animal. "Much more intakes of hypertonic saline compared with wild-type animals under water- and salt-depleted conditions" mentioned here means that, for example, in case of mice, the intake behavior in which the intake amount of 0.3 M saline after 24-h dehydration increases by 1.5-times or more, preferably by 2-times or more compared with that of the wild-type animals, preferably the littermate wild-type animals. Further, "the null mutant non-human animal whose function of $Na_v2$ genes is deficient on its chromosome" means the non-human animal whose endogenous genes that code for $Na_v2$ are inactivated by its destruction, deficiency, substitution or the like, so that the animal has lost its function of expressing $Na_v2$, and a rodent such as a mouse or a rat and the like is exemplified as a concrete example of the non-human animal, however, the non-human animal is not limited to the exemplification. In following explanation, a mouse is cited as an example of the non-human animal.

Any constructing method of $Na_v2$ knockout mice will suffice as long as it can construct the knockout mice that have lost the function of expressing $Na_v2$. For instance, the following method is exemplified; the genomic DNA library of mice is screened by using cDNA that codes for rat NaG, which is the species counterpart of mice $Na_v2$, as a probe, then an $Na_v2$ gene of genomic DNA is isolated, subsequently a targeting vector is constructed by inserting a marker gene such as neo gene or the like into the exon of $Na_v2$, and thus constructed vector is induced to ES cells by electroporation method, then homologously recombined ES cells are selected, and germ line chimeric mice are constructed with this ES cells strain, and they are intercrossed with the wild-type mice, then the heterozygous mutant mice (F1: first filial generation) are obtained, and by intercrossing of those heterozygous mutant mice, wild-type mice, which are littermates of $Na_v2$ knockout mice generated according to Mendelian ratio, can be generated.

The protein acting as a sensor of extracellular sodium ion level of the present invention is not particularly limited as long as it acts as a sensor of sodium ion level in nerve cells of the brain. For example, $Na_v2$ shown in Seq. ID No. 3 (GenBank accession number: L36179) or a protein comprised of amino acid sequence where one or a few amino acids are deficient, substituted, or added in amino acid sequence shown in Seq. ID No. 3 and acts as a sensor of extracellular sodium ion level, or a recombined protein of said proteins are concretely exemplified. Said protein acting as a sensor of extracellular sodium ion level can be prepared based on the DNA sequence information and the like by publicly known methods.

The genes of the invention that code for a protein acting as a sensor of extracellular sodium ion level include the gene that codes for $Na_v2$ shown in Seq. ID No. 3 in the sequence listing, for instance, $Na_v2$ gene shown in Seq. ID No. 2, gene DNA that codes for a protein comprised of amino acid sequence where one or a few amino acids are deficient, substituted, or added in amino acid sequence shown in Seq. ID No. 3, and the DNA that hybridizes with these gene DNAs under the stringent conditions and codes for the protein acting as a sensor of extracellular sodium ion level. These genes can be prepared based on the DNA sequence information and the like, for example with genomic library of mice constructed from cell line R1, 129/SvJ mice gene library or the like, by publicly known methods.

It is also possible to obtain DNA of the target that codes for a protein acting as a sensor of extracellular sodium ion level, such as human $Na_v2.1$ (GenBank accession number: M91556), rat NaG/SCL11 (GenBank accession number: Y09164) and the like, which have the same effect as $Na_v2$ genes, by hybridizing DNA library derived from mice under the stringent conditions, with a base sequence shown in Seq. ID No. 2 or its complimentary sequence and a part or whole of those sequences as a probe, and subsequent isolation of DNA that hybridizes said probe. As conditions of the hybridization to obtain said DNA, for instance, a hybridization at 42° C. and a rinsing treatment in buffer including 1×SSC and 0.1% SDS at 42° C., and more preferably, a hybridization at 65° C. and a rinsing treatment in buffer including 1×SSC and 0.1% SDS at 65° C. are exemplified. As factors influential in the stringency of a hybridization, there are various factors besides the above-mentioned temperature condition, and it is possible for a person skilled in the art to realize a same stringency as the above-illustrated stringency of the hybridization by combining those various factors appropriately.

The fusion protein of the present invention is defined as a protein constructed by combining a protein acting as a sensor of extracellular sodium ion level, such as $Na_v2$ and the like, and a marker protein and/or a peptide tag. As a marker protein, any of conventionally known marker protein will suffice, for example, alkaline phosphatase, Fc region of antibodies, HRP, GFP and the like are concretely exemplified, and as a peptide tag of the present invention, conventionally known peptide tag such as Myc tag, His tag, FLAG tag, GST tag and the like are concretely exemplified. Said fusion proteins can be constructed by a usual method, and are useful as an investigational reagent in the field concerned such as the purification of a protein acting as a sensor of extracellular sodium ion level utilizing the affinity between Ni-NTA and His tag, the detection of said protein, the quantification of an antibody to said protein and the like.

As an antibody of the present invention that specifically combines with a protein acting as a sensor of extracellular sodium ion level, an immunospecific antibody such as a monoclonal antibody, a polyclonal antibody, a chimeric antibody, a single stranded antibody, a humanized antibody and the like are concretely exemplified. Though these antibodies can be constructed by a usual method with the above-mentioned protein acting as a sensor of extracellular sodium ion level as an antigen, a monoclonal antibody is more preferable among them because of its specificity. Said antibody that specifically combines with a protein acting as a sensor of extracellular sodium ion level, such as a monoclonal antibody or the like, is useful, for instance, for the diagnosis of diseases caused by mutation or deficiency of $Na_v2$ such as chronic diseases of human caused by excessive intake of salt, and for elucidation of molecular mechanism of a protein such as $Na_v2$ or the like acting as a sensor of extracellular sodium ion level.

An antibody to a protein acting as a sensor of extracellular sodium ion level is developed by administering fragments containing a protein acting as a sensor of extracellular sodium ion level or its epitope, or cells that express said protein on the surface of the membrane to animals (preferably excluding human) with usual protocol. For instance, a polyclonal antibody can be prepared by immunizing a rabbit or the like with an antigen peptide as an immunogen, constructing antiserum by a usual method, and then purifying the constructed antiserum by a column in which the peptide used as the immunogen is fixed. Further, in preparation of a monoclonal antibody, any method that brings antibodies developed by cultured materials of continuous cell line, such as hybridoma method (Nature 256, 495–497, 1975), trioma method, human B-cell hybridoma method (Immunology Today 4, 72, 1983), and EBV-hybridoma method (MONOCLONAL ANTIBODIES AND CANCER THERAPY, pp. 77–96, Alan R. Liss, Inc., 1985) can be used. Followings are the explanation of the method of constructing a monoclonal antibody that specifically combines with $Na_v2$ derived from mice, that is, an anti-$mNa_v2$ monoclonal antibody, with an example of $Na_v2$ derived from mice as a protein acting as a sensor of extracellular sodium ion level.

The above-stated anti-$mNa_v2$ monoclonal antibody can be developed by cultivating an anti-$mNa_v2$ monoclonal antibody developing hybridoma in vivo or in vitro by a usual method. For instance, said anti-$mNa_v2$ monoclonal antibody is available through cultivation inside abdominal cavity of rodents, preferably mice or rats, in vivo, and through cultivation on a culture medium for animal cells in vitro. As examples of a medium for cultivating hybridoma in vitro, some cell culture mediums, such as RPMI1640, MEM or the like, which contain antibiotics like penicillin, streptomycin or the like are exemplified.

Anti-$mNa_v2$ monoclonal antibodies developing hybridoma can be constructed, for example, by the following procedures. First, BALB/c mice are immunized by using $Na_v2$ derived from mice or the like, then spleen cells and mouse NS-1 cells (ATCC TIB-18) of the immunized mice are fused by a usual method, and then screened by immunofluorescence staining pattern. As methods of separating and purifying said monoclonal antibodies, any method generally used to purify a protein will suffice, and liquid chromatography such as affinity chromatography and the like are concretely exemplified.

In order to develop a single stranded antibody to a protein acting as a sensor of extracellular sodium ion level of the present invention, the preparation method of single stranded antibodies (U.S. Pat. No. 4,946,778) can be applied. Further, in order to express a humanized antibody, it is possible to use transgenic mice, other mammalian animals or the like, and to isolate and identify the clones that express a protein acting as a sensor of extracellular sodium ion level with the above-mentioned antibodies, and to purify the polypeptide by affinity chromatography. An antibody to a protein acting as a sensor of extracellular sodium ion level is useful for elucidating the molecular mechanism of a protein acting as a sensor of extracellular sodium ion level.

It is possible to analyze the function of said protein acting as a sensor of extracellular sodium ion level by using the above-mentioned antibodies such as anti-$mNa_v2$ monoclonal antibodies and the like labeled with fluorescent materials like FITC (fluorescein isothiocyanate), tetramethylrhodamine isothiocyanate or the like; with radioisotopes such as $^{125}I$, $^{32}P$, $^{14}C$, $^{35}S$, $^3H$ or the like; or with enzymes like alkaline phosphatase, peroxidase, β-galactosidase, phycoerythrin or the like; or by using fusion proteins where anti-$mNa_v2$ monoclonal antibodies are fused with fluorescence emission proteins such as green fluorescent protein (GFP) or the like. Examples of the immunoassays include RIA method, ELISA method, fluorescent antibody technique, plaque method, spot method, hemagglutination reaction method, Ouchterony method and the like.

This invention relates to a host cell which contains an expression system that can express a protein acting as a sensor of extracellular sodium ion level. The gene that codes for a protein acting as a sensor of extracellular sodium ion level can be introduced into a host cell by a number of methods described in standard laboratory manuals by Davis et al. (BASIC METHODS in MOLECULAR BIOLOGY, 1986), and by Sambrook et al. (MOLECULAR CLONING: A LABORATORY MANUAL, 2nd Ed., Cold Spring Harbor Laboratory Press, Cold Spring Harbor, N. Y., 1989), and the like. Examples of those methods include calcium phosphate transfection, DEAE-dextran-mediated transfection, transvection, microinjection, cationic liposome-mediated transfection, electroporation, transduction, scrape loading, ballistic introduction and infection. Examples of the host cells include bacterial procaryotic cells such as *Escherichia coli, Streptomyces, Bacillus subtilis, Streptococcus, Staphylococcus* and the like; fungous cells such as yeast, *Aspergillus* and the like; insect cells such as drosophila S2, spodptera Sf9 and the like; and animal or plant cells such as L cells, CHO cells, COS cells, HeLa cells, C127 cells, BALB/c3T3 cells (including mutant strains deficient in dihydrofolate reductase, thymidine kinase or the like), BHK21 cells, HEK293 cells, Bowes melanoma cells, oocytes and the like.

As the expression system, any expression system that can express a protein acting as a sensor of extracellular sodium ion level in a host cell will suffice. Examples of the expression system include expression systems derived from chromosome, episome and virus, for example, vectors derived from bacterial plasmid, yeast plasmid, papovavirus like SV40, vaccinia virus, adenovirus, chicken pox virus, pseudorabies virus, or retrovirus, vectors derived from bacteriophage, transposon, and the combination of these, for instance, vectors derived from genetic factors of plasmid and of bacteriophage such as cosmid or phagemid. These expression systems may contain regulatory sequence that acts not only as a promoter but also as a controller of expressions.

A host cell that contains the above-mentioned expression system, cell membrane of said host cell, and a protein acting as a sensor of extracellular sodium ion level which is obtainable by the cultivation of said host cell can be used in the screening method of the present invention as hereinafter described. For example, the method of F. Pietri-Rouxel et al. (Eur. J. Biochem., 247, 1174–1179, 1997) or the like can be used as the method to obtain cell membranes, and publicly known methods including ammonium sulfate or ethanol precipitation, acid extraction, anion or cation exchange chromatography, phosphocellulose chromatography, hydrophobic-interaction chromatography, affinity chromatography, hydroxyapatite chromatography, and lectin chromatography, preferably high-speed liquid chromatography can be used to pick up said protein acting as a sensor of extracellular sodium ion level from cell cultured material and purify it. As columns used for affinity chromatography, in particular, there are columns to which an antibody to a protein acting as a sensor of extracellular sodium ion level such as an anti-$Na_x2$ monoclonal antibody and the like is bound, or in case that normal peptide tag is added to said protein such as $Na_x2$ or the like acting as a sensor of extracellular sodium ion level, there are columns to which materials having affinity to the peptide tag are bound. These proteins acting as sensors of extracellular sodium ion level can be obtained by using these columns.

In the present invention, transgenic non-human animal that excessively expresses a gene that codes for a protein acting as a sensor of extracellular sodium ion level is defined as non-human animal that produces larger amount of a protein acting as a sensor of extracellular sodium ion level than wild-type non-human animal does. Though concrete examples of a non-human animal of the present invention include rodents, such as rabbits, mice, rats and the like, a non-human animal of the present invention is not limited to these animals.

Homozygous non-human animals generated according to Mendelian ratio include excessive expression type that excessively expresses a protein acting as a sensor of extracellular sodium ion level and the littermate wild-type, and it is possible to carry out precise comparative experiments in individual level by using the excessive expression types and the littermate wild-types of these homozygous non-human animals at the same time. Therefore, it is preferable to use animals of the same species, more preferably the littermates, as the wild-type non-human animals, in other words, the non-human animals that excessively express a gene that codes for a protein acting as a sensor of extracellular sodium ion level together in, for example, the screening hereinafter described in the present invention. The generating method of the non-human animals that excessively express a gene that codes for a protein acting as a sensor of extracellular sodium ion level will be explained below, with an example of transgenic mice of a protein acting as a sensor of extracellular sodium ion level.

The transgenic mice of a protein acting as a sensor of extracellular sodium ion level can be generated in following procedures. A transgene is constructed by fusing promoters such as chicken β-actin, mouse neurofilament, SV40 or the like, and poly A or introns such as rabbit β-globin, SV40 or the like with cDNA that codes for a protein such as $Na_x2$ or the like acting as a sensor of extracellular sodium ion level. The transgene is microinjected in the pronucleus of a fertilized egg of a mouse, and the egg cell is cultured, then transplanted to the oviduct of a recipient mouse. After rearing up the recipient animal, baby mice that have the above-mentioned cDNA are selected from the mice born from the recipient animal. Thus transgenic mice can be generated. The baby mouse that has cDNA can be selected by extracting crude DNA from a tail or the like of a mouse, then carrying out methods like dot hybridization using a gene that codes for a protein acting as a sensor of extracellular sodium ion level as a probe, PCR method using a specific primer and the like.

By using a protein acting as a sensor of extracellular sodium ion level, a gene that codes for said protein, a fusion protein created by combining a protein acting as a sensor of extracellular sodium ion level and a marker protein and/or a peptide tag, an antibody to a protein acting as a sensor of extracellular sodium ion level, a host cell which contains an expression system that can express a protein acting as a sensor of extracellular sodium ion level, a non-human animal which excessively expresses a gene that codes for a protein acting as a sensor of extracellular sodium ion level, a null mutant non-human animal showing salt intake behavior similar to that of the wild-type animals under water-sufficient conditions and showing much more intakes of hypertonic saline compared with the wild-type animals under water- and salt-depleted conditions, a cell that expresses a protein acting as a sensor of extracellular sodium ion level, or the like, it becomes possible to screen a material that promotes or suppresses the function of a protein acting as a sensor of extracellular sodium ion level or a material that promotes or suppresses the expression of a protein acting as a sensor of extracellular sodium ion level. What obtained by this screening could be a suppressant, a preventive, or a remedy for chronic diseases of human resulted from excessive intake of salt, or substances useful for diagnosis and cure of the diseases resulted from deficiency or abnormality of a protein acting as a sensor of extracellular sodium ion level or the like.

Examples of said screening methods include a method with cells that express a protein acting as a sensor of extracellular sodium ion level and a subject material; a method with null mutant non-human animals of the present invention showing salt intake behavior similar to that of the wild-type animals under water-sufficient conditions and showing much more intakes of hypertonic saline compared with the wild-type animals under water- and salt-depleted conditions or transgenic non-human animals which excessively express a gene that codes for a protein acting as a sensor of extracellular sodium ion level, and the subject material.

As a screening method with cells that express a protein acting as a sensor of extracellular sodium ion level and a subject material is, a method wherein cells that express a protein acting as a sensor of extracellular sodium ion level and a subject material are brought into contact, and then the change of the function or the expression of a protein acting as a sensor of extracellular sodium ion level is measured/evaluated is exemplified.

Concrete examples of a screening method with the null mutant non-human animals showing salt intake behavior similar to that of the wild-type animals under water-sufficient conditions and showing much more intakes of hypertonic saline compared with the wild-type animals under water- and salt-depleted conditions or the transgenic non-human animals which excessively express a gene that codes for a protein acting as a sensor of extracellular sodium ion level and the subject material include; a method wherein nerve cells obtained from the null mutant non-human animals showing salt intake behavior similar to that of the wild-type animals under water-sufficient conditions and showing much more intakes of hypertonic saline compared with the wild-type animals under water- and salt-depleted conditions, or from the transgenic non-human animals which excessively express a gene that codes for a protein acting as a sensor of extracellular sodium ion level are brought into contact with a subject material in vitro, and then the change of the function or the expression of said protein is measured/evaluated; a method wherein saline is administrated to said null mutant non-human animals or to said transgenic non-human animals beforehand, then the nerve cells obtained from said non-human animals are cultured in the presence of the subject material, and the change of the function or the expression of said protein is measured/evaluated; a method wherein saline and a subject material are administrated to said null mutant non-human animals or to said transgenic non-human animals beforehand, then the change of the function or the expression of said protein in the nerve cells obtained from said non-human animals is measured/evaluated; a method wherein saline and a subject material are administrated to said null mutant non-human animals or to the transgenic non-human animals beforehand, then the change of the function or the expression of said protein in the non-human animals is measured/evaluated.

In measuring and evaluating the change of the function or the expression of a protein acting as a sensor of extracellular sodium ion level, it is preferable to evaluate/compare with the measured value of the wild-type non-human animals, in particular, of the littermate wild-type non-human animals, as control, because it offsets the dispersion caused by the difference between individuals. The function of a protein acting as a sensor of extracellular sodium ion level is to regulate sodium level of body fluid in vivo, that is, to act as a sensor of extracellular sodium ion level. Although concrete examples of the change of said function include the change of the function in the sensory circuits for body fluid osmolarity, the change in preference-aversion response to the intake of water and salt and the like, the change of the function is not limited to these examples.

The medical compounds of the present invention are not limited particularly as long as the medical compounds contain said protein of the present invention that acts as a sensor of extracellular sodium ion level, or materials that promote or suppress the function of a protein acting as a sensor of extracellular sodium ion level, or materials that promote or suppress the expression of a protein acting as a sensor of extracellular sodium ion level as their effective components, and these medical compounds can be used for the treatment of the patients who need promotion of the function or enhancement of the expression of a protein acting as a sensor of extracellular sodium ion level, or the patients who need suppression of the function or the expression of a protein acting as a sensor of extracellular sodium ion level.

The present invention will be explained in detail with embodiments below, but the technological scope of the present invention is not limited to these embodiments.

[Construction of a Targeting Vector]

In order to construct a targeting vector, genomic fragments of mice containing protein-coding exons 1, 2 and 3 were cloned by NaG/SCL11 probe of rats. Nine independent genomic clones were isolated from mouse genomic libraries (donated by Dr. Mori, Osaka Univ., Japan) prepared from a cell line R1, by hybridization with a 446-bp fragment of rat NaG cDNA (nucleotide residues 11–456 encompassing the first three coding exons: GenBank accession number Y09164: Seq. ID No. 1). By Southern blot analysis using several restriction enzymes, it has been confirmed that all these overlapping clones were derived from a single genomic locus. The hybridization-positive 3.2 and 3.7 kb HindIII fragments were subcloned into pBluescript II SK (−) (Stratagene) and subjected to DNA sequencing (the sequence is in GenBank under accession number AF190472: Seq. ID No. 4). The 3.2 kb fragment contained protein-coding exon 1 (13 bases of the 5' untranslated region and the first 238 bases in the mouse $Na_v2$ protein-coding sequence: nucleotide residues 238–490 of GenBank accession number L36179) and the 3.7 kb fragment contained exons 2 (nucleotide residues 491–609) and 3 (nucleotide residues 610–701). The DNA sequence encoding the three exons was identical to that of mouse $Na_v2.3$ cDNA cloned by Tamkun and coworkers (J. Biol. Chem. 269, 30125–30131 (1994)). The cloned genomic fragments showed identical restriction maps with mouse genomic DNA on Southern blot analysis with four restriction enzymes (BamH I, Bgl II, EcoR I and Hind III). This finding indicates that mouse $Na_v2.3$ is the species counterpart of rat NaG. Accordingly, $Na_v2.3$, NaG and SCL11 are designated as $Na_v2$.

In order to construct the targeting vector, the lacZ gene was so designed that it would be inserted into the protein-coding exon 1 of the mouse $Na_v2$ gene and that the N-terminal twenty amino-acid sequence of mouse $Na_v2$ would be fused with β-galactosidase. In other words, the 12.5 kb Sal I fragment containing the three exons was inserted into the Xho I site of PDT-A (Anal. Biochem. 214, 77–86 (1993)), then the Sal I-Xho I fragment of the lacZ-neo cassette was introduced into the endogenous Xho I site located in exon 1 (see FIG. 1a). This results in the expression of a protein that fuses the first 20 amino acids of the mouse $Na_v2$ protein with the N-terminus of β-galactosidase. The original genomic structure of mouse $Na_v2$ gene was not modified except for the insertion of the lacZ-neo cassette to make sure that the lacZ gene is expressed in place of the mouse $Na_v2$ gene in the targeted mice. An EcoR I linker was inserted beforehand into the 5' terminus of the lacZ-neo cassette to utilize it as an exogenous restriction site in Southern blot screening analysis. FIG. 1a shows restriction maps of the targeting vector (top), mouse $Na_v2$ gene locus of wild-types (middle), and recombinant gene locus (bottom). In FIG. 1a, restriction sites B, Bg, E, H, and X represent BamH I, Bgl II, EcoR I, Hind III and Xho I respectively.

[Generation of $Na_v2$ Knockout Mice]

The above-mentioned filamentous shaped targeting vector was induced into ES cells (R1 cell line derived form 129/SV mouse) by an electroporation method. According to the method described in the paper (Neurosci. Lett. 247, 135–138 (1998)), neomycin-resistant ES clones were selected by G418, and screening of the targeted clones were performed. Homologous recombination was verified by Southern blot analysis using EcoR I digestion with probe 1 (see FIG. 1a; the 0.3 kb EcoR I-Xba I fragment located about 8 kb upstream from the Xho I site in exon 1). The selected clones were checked using probe 2 (the 0.6 kb Pst I fragment derived from the neo gene). The targeted locus was verified by genomic PCR using one sense primer (primer 1, ATGT-TGACTTCCCCAGAGCC in the 5'-terminal region of exon 1, Seq. ID No. 5) and two antisense primers (primer 2, AACCAGGCAAAGCGCCATTC in the 5'-terminal region of lacZ, Seq. ID No. 6: primer 3, CATCTTC-CAAGGGCTCTGACA in the 3'-terminal region of exon 1, Seq. ID No. 7). PCR amplification was carried out in two stages with EX-Taq polymerase (Takara) according to the manufacturer's protocol using a programmable thermal cycler (first stage; 95° C. for 5 minutes, 60° C. for 1 minute, 72° C. for 1 minute: second stage; 95° C. for 30 seconds, 60° C. for 30 seconds, 72° C. for 1 minute).

Two out of 98 ES clones, which were identified to have the correct homologous recombinant allele, were used for injection into eight-cell stage C57BL/6J mouse embryos. The injected embryos were cultured in M16 medium overnight up to blastocysts, and seven to ten blastocysts were transplanted into the uterus of a recipient ICR mouse. The male chimeric mice thus obtained were mated with C57BL/6J females, and heterozygous mice (F1: first filial generation) were generated from littermates, and this heterozygous mutant mice were intercrossed subsequently in order to obtain homozygous mice, then $Na_v2$ deficient mice, which were produced according to Mendelian ratio, were generated.

The null mutant animals (mouse $Na_v2^{-/-}$) were healthy, fertile and apparently normal. The genotypic analysis of 458 four-week-old offspring obtained from breeding heterozygous animals showed an approximately Mendelian ratio between wild-type (29.5%, n=135), heterozygous mutant (48.2%, n=221) and homozygous mutant (22.3%, n=102) animals. This suggests that embryonic development and body functions were not significantly impaired in either heterozygous or homozygous mutant animals. It was reported that acute and transient expression of mouse $Na_v2$ was induced perinatally to the uterine smooth muscle (J. Biol. Chem. 269, 30125–30131 (1994), Am. J. Physiol. 270, C688–696 (1996)). It should be noted that pups were delivered normally in $Na_v2^{-/-}$ mice. The pattern of lacZ expression in the null mutants was identical to that in the heterozygous mutants except for the intensity of the expression, suggesting that deficiency of mouse $Na_v2$ does not affect the differentiation or viability of the mouse $Na_v2$-expressing cells.

FIG. 1b shows the result of Southern blot analysis in which samples of genomic DNA were derived from tails of wild-type (+/+), heterozygous (+/-), and homozygous (-/-) mice, and then membranes blotted with genomic DNA digested with EcoR I were hybridized with said probe 1 located on the 5' side of the targeting vector. The sizes for the wild-type (18 kb) and recombinant (10 kb) genotypes are shown on the right of FIG. 1b. FIG. 1c shows the result of genomic PCR analysis of wild-type (+/+), heterozygous (+/-), and homozygous (-/-) mutant mice. The sizes for the wild-type (200 bp) and recombinant (400 bp) genotypes are shown on the right of FIG. 1c.

[Confirmation of Non-expression of $Na_v2$ in $Na_v2$ Knockout Mice]

The mouse $Na_v2$ protein expression in the mutant mice was examined by Western blot analysis. Lung tissue samples of each wild-type (+/+), heterozygous (+/-), and homozygous (-/-) mice were prepared according to the methods of Knittle et al. (Am. J. Physiol. 270, C688–696 (1996)). SDS-polyacrylamide gel electrophoresis and immunoblotting were carried out according to the method described in the paper (Neurosci. Lett. 247, 135–138 (1998)). Anti-mouse-$Na_v2.3$ antiserum (a generous gift from Dr. M. Tumkun, Colorado State Univ., CO) was used at a 1:500 dilution in PBS. The immunoblots were incubated with several non-immune sera to verify that it was not non-specific combination. The results are shown in FIG. 1d. The position of $Na_v2$ protein (220 kDa) is indicated on the right of FIG. 1d. The sodium channel gave a broad signal, since $Na_v2$ protein is highly glycosilated and readily aggregates even in the SDS-containing buffer. Compared with wild-type mice, about a half of the amount of mouse $Na_v2$ protein in heterozygous mutant ($Na_v2^{+/-}$) mice, and no mouse $Na_v2$ protein in homozygous mutant ($Na_v2^{-/-}$) mice was detected in lung membrane preparations. It is indicated that the allele was a null mutation because mouse $Na_v2$ protein was not expressed.

[Confirmation of the Expression of lacZ in $Na_v2$ Knockout Mice by X-Gal Staining]

Figure 2:
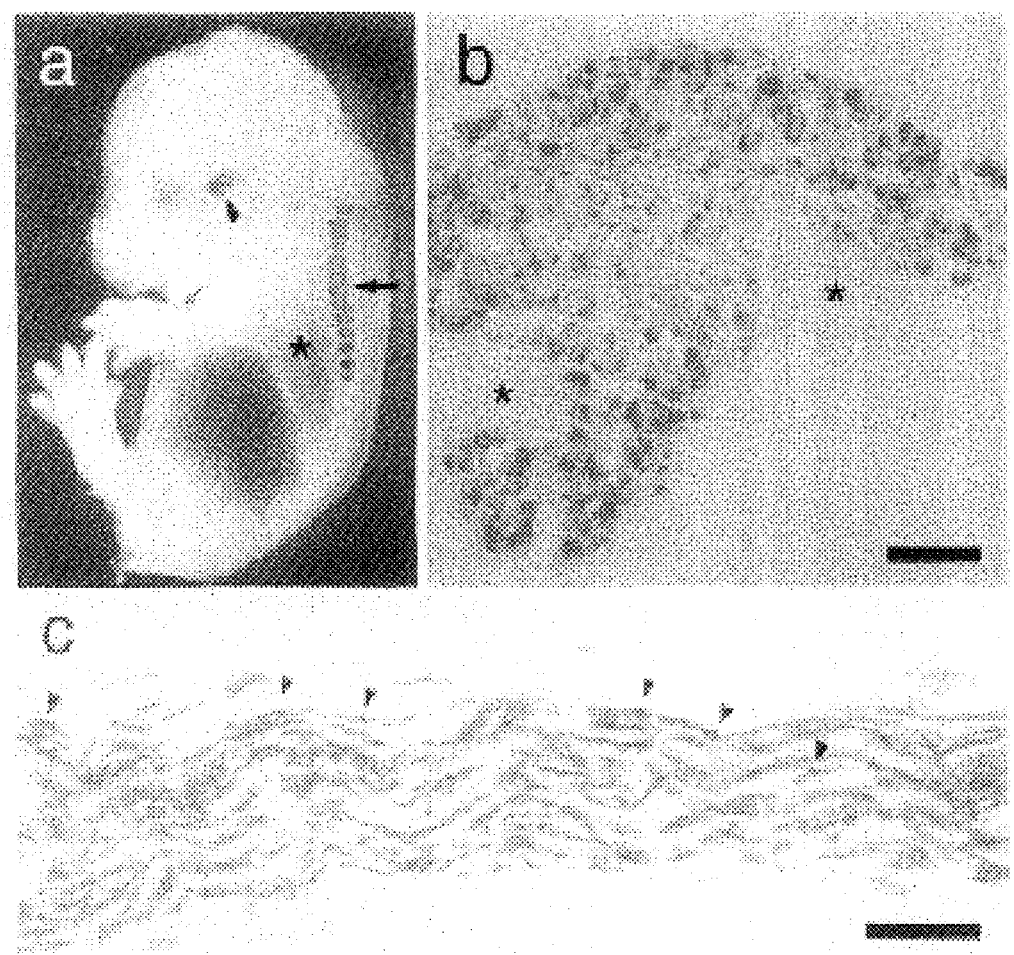
FIG. 2 is a view showing lacZ-expressing areas in embryos, dorsal root ganglia and the thoratic regions of $Na_v2$ knockout mice of the present invention.

Embryos were fixed by immersion in 3.5% formaldehyde in PBS for 1 hour at room temperature, and then cut midsagittally with a razor. FIG. 2a shows X-Gal staining of a whole-mount mouse $Na_v2+/-$ embryo at embryonic day 15 (E15). Intensive β-galactosidase activity was observed in the trigeminal ganglia (pointed by the arrowhead in FIG. 2a) and dorsal root ganglia (pointed by the arrow in FIG. 2a)(see reference photograph 1). In this E15 mouse, lacZ-expression was evident also in the lung (pointed by the asterisk). In these organs, the expression of lacZ persisted into adulthood. When dorsal root ganglia were cut into thin sections after X-Gal staining, β-galactosidase activity was detected in spinal sensory neurons with various cellular diameters. An X-Gal stained cryostat tissue section of dorsal root ganglion of postnatal day 2 $Na_v2^{+/-}$ mouse was shown in FIG. 2b (see reference photograph 1). The expression of lacZ was confined to the somata of neurons within dorsal root ganglion (nerve tracts are shown by asterisk in FIG. 2b), and not detected in axons. A similar pattern of lacZ expression was observed in tissue sections of the trigeminal ganglia. A cryostat section of adult sympathetic nerve trunk in the thoracic region is shown in FIG. 2c (see reference photograph 1). Based on the appearance, distribution, and size of the cell bodies, the numerous intensely stained cells are likely to be Schwann cells. The expression of lacZ was also observed in cardiac autonomic nerves and lingual nerves. These patterns of lacZ expression agreed well with the results of rat $Na_v2$ and mouse $Na_v2$ expressions (Proc. Natl. Acad. Sci. USA 89, 7272–7276(1992), FEBS Lett. 400, 183–187 (1997), Glia, 21, 269–276 (1997)). This indicates that the lacZ gene expression is duly under the control of the regulatory regions of mouse $Na_v2$ gene. In FIG. 2c, the arrowheads identify the somata of Schwann cells, and scale bar=50 μm.

[Physiological Roles of $Na_v2$]

Figure 3:
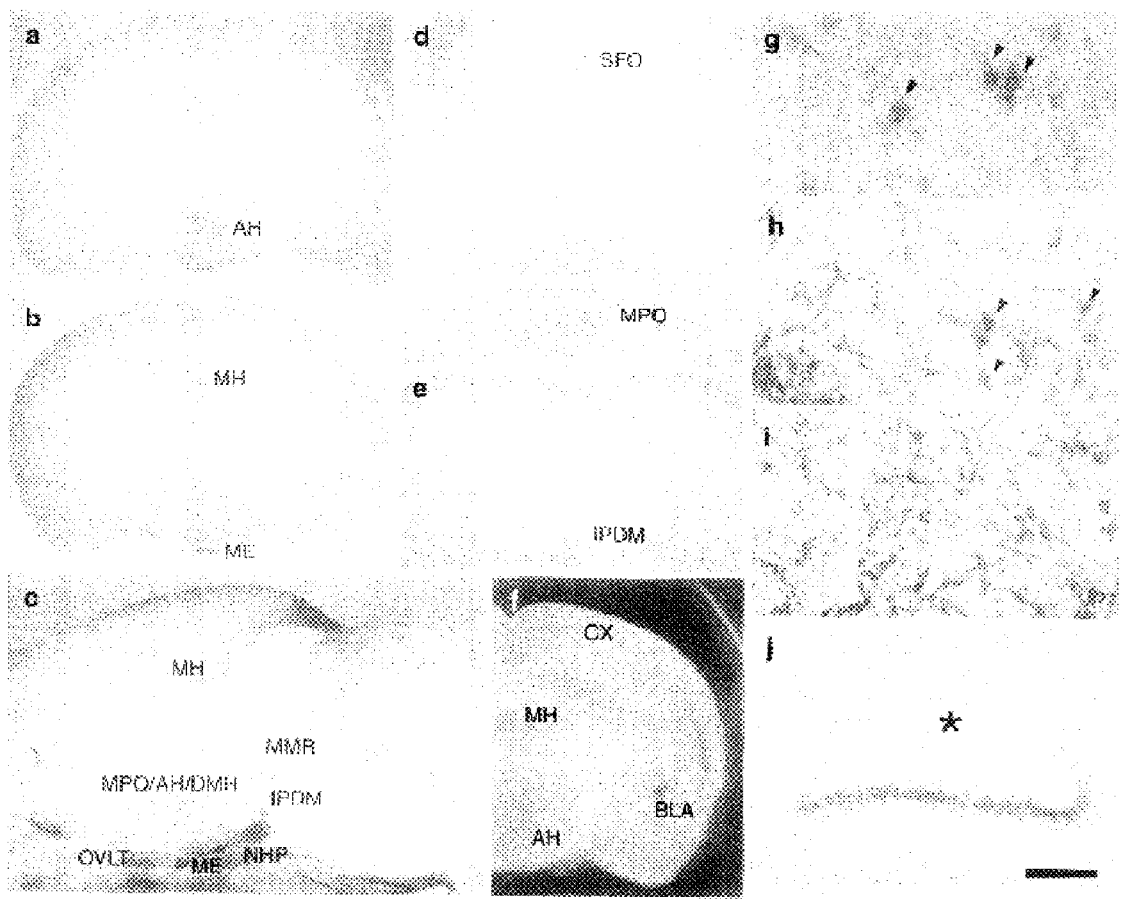
FIG. 3 is a view showing lacZ-expressing areas in the brains of $Na_v2$ knockout mice of the present invention.

In order to examine the physiological roles of mouse $Na_v2$, the lacZ-expression was surveyed throughout central nervous system (CNS) using brains of $Na_v2^{+/-}$ and $Na_v2^{-/-}$ mice. Postnatal animals were perfused under pentobarbital anesthesia first with PBS and then with the fixative. The fixed brains were cut coronally at 2 mm thick or sagittally with a razor. Samples were rinsed twice with PBS and incubated overnight in PBS containing 1 mg/ml X-Gal, 5 mM $K_3Fe(Cn)_6$, 5 mM $k_4Fe(CN)_6$, 2 mM $MgCl_2$, and 0.2% NP-40 at 37° C. For immunostaining, some X-Gal stained slices were cut further into coronal sections at 14 μm thick with a cryostat microtome and mounted onto gelatin-coated slides. With rabbit polyclonal antibodies to anti-neurofilament 200 (Sigma, N-4142) or to anti-glial fibrillary acidic protein (GFAP) (Santa Cruz Biochemistry, sc-6170), immunostaining was performed (Neurosci. Lett. 247, 135–138 (1998)). FIG. 3 shows that mouse $Na_v2$ was expressed in specialized neurons and ependymal cells in the adult CNS (see reference photograph 2).

In FIG. 3, lacZ expression in the CNS of $Na_v2^{+/-}$ (FIGS. 3a–e) and $Na_v2^{-/-}$ (FIG. 3f) mutant mice were shown. Fixed adult brains were cut coronally (FIGS. 3a, b, d, e and f) or midsagittally (FIG. 3c) at 2 mm and then stained with X-Gal. In (FIG. 3c), the skull under the brain was not removed. In (FIG. 3e), homozygous mutant mice were used for the analysis to detect the locus of low level expression. Explanations of the abbreviations in FIG. 3 are as follows: AH, anterior hypothalamic area; MH, medial habenular nucleus; ME, median eminence; OVLT, organum vasculosum laminae terminalis; MPO, medial preoptic area; DMH, dorsomedial hypothalamus; IPDM, interpeduncular nucleus of the dorsomedial part; MMR, medial part of the median raphe; NHP, neurohypophysis; SFO, subformical organ; CX, cerebral cortex; BLA, basolateral amygdala. In (FIG. 3c), OVLT was removed from the central nervous system and attached to the skull. The coronal semi-whole-mount brains were cut 50 μm thick using cryostat microtome and then stained with anti-neurofilament polyclonal antibodies (FIGS. 3g and h), anti-GFAP polyclonal antibodies (FIG. 3i), or cresyl violet (FIG. 3j). Brown signals are the site that reacted with the antibodies. The samples are AH (FIG. 3g), SFO (FIGS. 3h and i) and ME (FIG. 3j). Arrowheads indicate double positive neurons. The asterisk in FIG. 3j indicates the third ventricle. The dorsal side is toward the top of the panels. Scale bar: FIG. 3g to FIG. 3h=30 μm; FIG. 3j=100 μm.

As shown in FIG. 3, clusters of lacZ expression were limited to specific loci in the central nervous system (FIGS. 3a–f): MPO, AH, DMH, IPDM, MMR, MeV, MH, ME, SFO, OVLT and NHP. ME, SFO, OVLT and NHP are known as the circumventricular organs (CVOs) having unusual dense and permeable capillary networks that facilitate secretion of substances into blood or penetration of substances into important tissue (FASEB J, 7, 678–686 (1993)). Relatively weak lacZ expression was detected in CX and BLA in $Na_v2^{+/-}$ mice. The intensity of the lacZ expression in these areas was more evident in $Na_v2^{-/-}$ mice (FIG. 3f). To examine the cell-types expressing lacZ, the brains were stained with X-Gal and cut into tissue sections with a cryostat microtome and subsequently immunostained with anti-neurofilament polyclonal antibodies or anti-glial fibrillary acidic protein (GFAP) polyclonal antibodies, or stained with cresyl violet. Most of the cells expressing lacZ were positive for neurofilament in the MPO, AH (FIG. 3g), IPDM, MMR, MH and MeV. GFAP-positive cells were negative for the lacZ expression, suggesting that astrocytes are negative for mouse $Na_v2$.

The distribution of lacZ-expressing cells in the CVOs was of particular interest. In the ME, the lacZ-expressing cells lined the floor of the third ventricle (FIG. 3j). This distribution corresponds to the location of nonciliated ependymal cells. These cells are thought to be tanycytes, which are characteristic cells providing a morphological connection between cerebrospinal fluid (CSF), nerve cells and blood vessels (Neuroscience 3, 277–283 (1978)). They are thought to be involved in exchange of substances between the CSF and pericapillary space. The lacZ-positive cells were sparsely distributed all over the SFO, and most of them were co-localized with neurofilaments (FIG. 3h) and negative for GFAP (FIG. 3i). Intensive lacZ-positive cells also populated lining the entire third ventricle, suggesting that they are ependymal cells. In the NHP, the X-Gal signals were densely clustered. They are likely to correspond to so-called pituicytes (J. Exp. Biol. 139, 67–79 (1988)).

[Fos-immunohistochemistry]

Since analysis of the lacZ expression clearly demonstrated that mouse $Na_v2$ was expressed in the four CVOs and several nuclei in the central nervous system and that the mouse $Na_v2$-expressing cells were thus diverse not only in tissue distribution but also in cell types, it became difficult to obtain a unified view of channel function or property. However, the four CVOs are thought to be involved in body-fluid homeostasis (FASEB J, 7, 678–686 (1993), Annu. Rev. Physiol. 59, 601–619 (1997), Physiol. Rev. 78, 583–686 (1997), Physiol. Rev. 58, 582–603 (1978), Ann. NY Acad. Sci, 877, 258–280 (1999)). If the mouse $Na_v2$ channel functions in the sensory circuits for body-fluid osmolarity, it was expected that the activity and gene expression in these organs would be affected in the mouse $Na_v2$ mutant mice. Therefore, the effects of water deprivation on the central expression of Fos, a nuclear protein and a marker of changes in neural activity in response to the extracellular fluid balance in mice and rats, were examined as follows.

Figure 4:
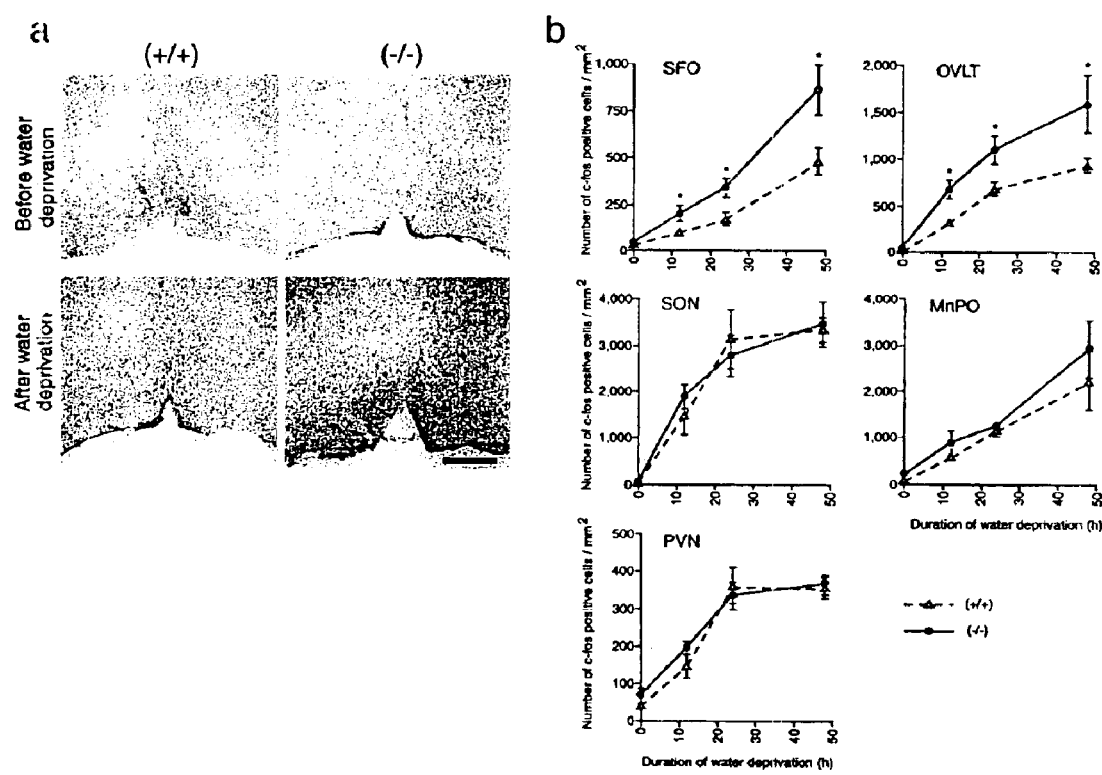
FIG. 4 is a view showing the result of the influence of dehydration on the expression of a nuclear protein, Fos, in $Na_v2$ knockout mice of the present invention.

The time course of changes in Fos-immunopositive cell density in five regions of the brain (the medial preoptic nucleus (MnPO), organum vasculosum laminae terminalis (OVLT), subformical organ (SFO), paraventricular nucleus (PVN), and supra optic nucleus (SON)) under water-sufficient and water-depleted conditions were examined with mice which were deprived of water for 0 h (n=4 for mouse $Na_v2^{+/+}$, n=4 for mouse $Na_v2^{-/-}$), 12 h (n=5 and 5), 24 h (n=6 and 7), or 48 h (n=6 and 5). The mice were perfused with the fixative as described above, and their brains were immersed in the same fixative at 4° C. overnight. Brains were cut coronally into sections at 50 μm thick on a vibratome (Leica, VT1000S). Immunostaining was performed with a goat anti-Fos polyclonal antibody (Santa Cruz Biochemistry, sc-52-G) at a dilution of 1:1000 in PBS. Sections containing regions of interest were chosen and the Fos-immunopositive nuclei were enumerated. Each area was measured by using an image analysis system (KS400 attached to Axiophoto 2). The number of nuclei present per $mm^2$ was determined in the above-mentioned five regions of the brain. The results are shown in FIG. 4 (see reference photograph 3).

FIG. 4a is typical examples of tissue sections containing the OVLT derived from wild-type (+/+) and null mutant (−/−) mice under water-sufficient or 24-h dehydrated condition. Scale bar=200 μm. In FIG. 4b, mean numbers of Fos-immunopositive cells per $mm^2$ in subformical organ (SFO), supra optic nucleus (SON), paraventricular nucleus (PVN), organum vasculosum laminae terminalis (OVLT) and the median preoptic nucleus (MnPO) during water deprivation were plotted. The vertical bars indicate S. E., the asterisk shows that a significant difference (P<0.05) between $Na_v2^{-/-}$ and $Na_v2^{+/+}$ mice were revealed. In the water-sufficient condition, Fos-immunopositive cells were not detected in any region examined. At 12, 24 and 48 h after water deprivation, number of cells with Fos-immunopositive nuclei was remarkably increased in these regions in both $Na_v2^{-/-}$ and $Na_v2^{+/+}$ mice. However, in SFO and OVLT, approximately two-fold increases in Fos-immunopositive nuclei were observed in $Na_v2^{-/-}$ mice as compared with in $Na_v2^{+/+}$ mice. In the MnPO, PVN and SON, on the other hand, the rates of increase in Fos-immunopositive cells were comparable between the two groups.

[Behavioral Analysis]

Figure 5:
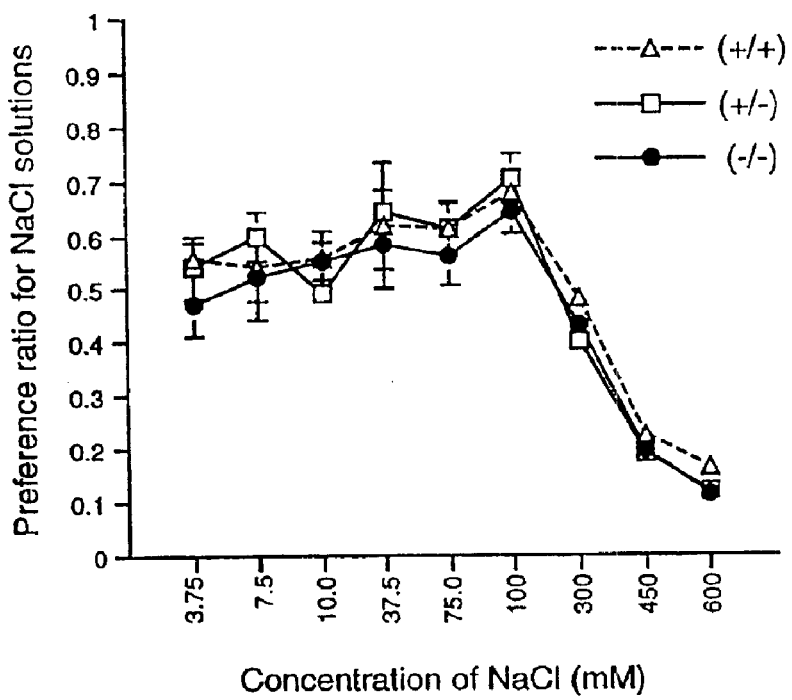
FIG. 5 is a view showing the result of the influence of mouse $Na_v2$ channel deficiency of the present invention to water and salt intake of mice.
Figure 5:
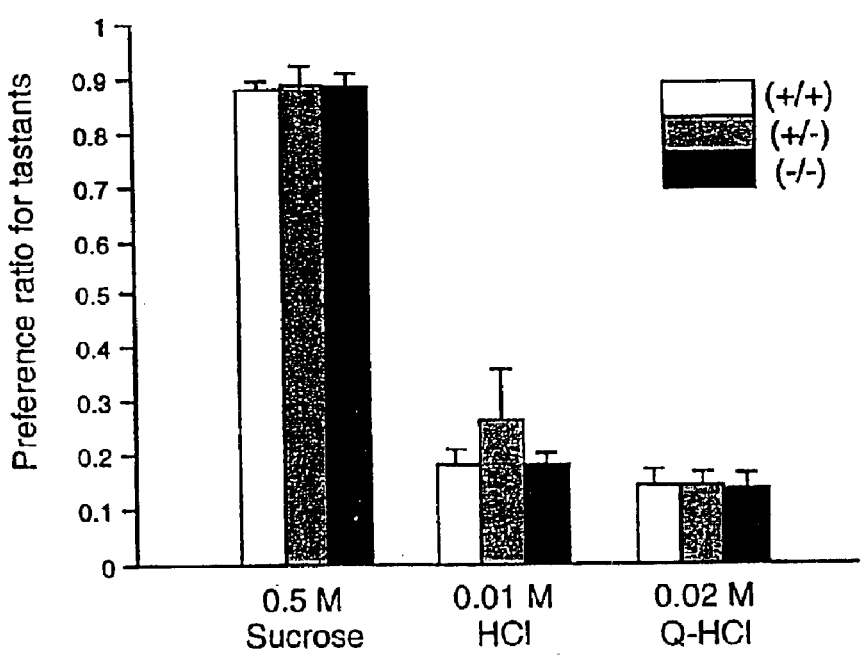

The effect of mouse $Na_v2$-channel deficiency on water and salt intakes of mice was next examined. For the behavioral study, the mutant mice were backcrossed with C57 BL/6J males. As a result, it was verified that the behavior of F1 and F4 mice was identical. The preferance-aversion behavior of the homozygous-, heterozygous-mutant and wild-type littermates were measured by a 48-h two-bottle preference test. Mice were presented with a choice between distilled water and a tasting solution for 48 h in their home cage. For all behavioral studies, male mice at 12–24 weeks of age were used. They are individually housed under constant room temperature, humidity and 12/12 h light-dark cycle. The positions of the two bottles were switched every 24 h to avoid side preference. The total intake for each animal was measured and used to calculate a preference ratio according to the following formula: preference ratio= volume of tasting solution (ml)/total intake volume of tasting solution and water (ml). The results are shown in FIG. 5. Preference ratios for NaCl solutions with a series of concentrations are shown in FIG. 5a, and that for three fundamental tastants with fixed concentrations are shown in FIG. 5b. Homozygous (−/−), heterozygous (+/−) and wild-type (+/+) mice, five mice each, were used here. FIG. 5a shows that the concentration sensitivity to a series of NaCl solutions was comparable among the three groups of mice under the condition satiated with water and salt, and all the groups showed maximum preference to 0.1 M NaCl and evasiveness to 0.3 M or higher concentration of NaCl. The null mutants showed normal preferences to various tastants under the condition satiated with water and salt. FIG. 5b shows that preference ratios to sweet (0.5 M sucrose), sour (0.01 M HCl) and bitter (0.02 M quinine hydrochloride) tasters were not different among the groups.

[Electrophysiology]

To verify the normality in taste responses in the null mutants, electrophysiological analysis was performed on the chorda tympani nerve, which is known to be the nerve fiber responsible for tasting NaCl. Male mice at 12–24 weeks of age were used (4 wild-type and 5 homozygous mice for the normal condition; 3 wild-type and 5 homozygous mice for the acute salt-appetite condition). Each mouse was deeply anesthetized by an intraperitoneal injection of sodium pentobarbital (60 mg/kg), then tracheotomized and secured with a head holder. The chorda tympani nerve was exposed, freed from surrounding tissues, and cut at the point of its entry to the bulla. The whole bundle of the nerve was dissected and lifted on a platinum wire recording electrode (0.1 mm in diameter). An indifferent electrode was attached to nearby tissue. The nerve activities were amplified, displayed on an oscilloscope, and monitored with an audioamplifier. The amplified signal was passed through an integrator with a time constant of 0.3 sec and was displayed on a slipchart recorder.

Figure 6:
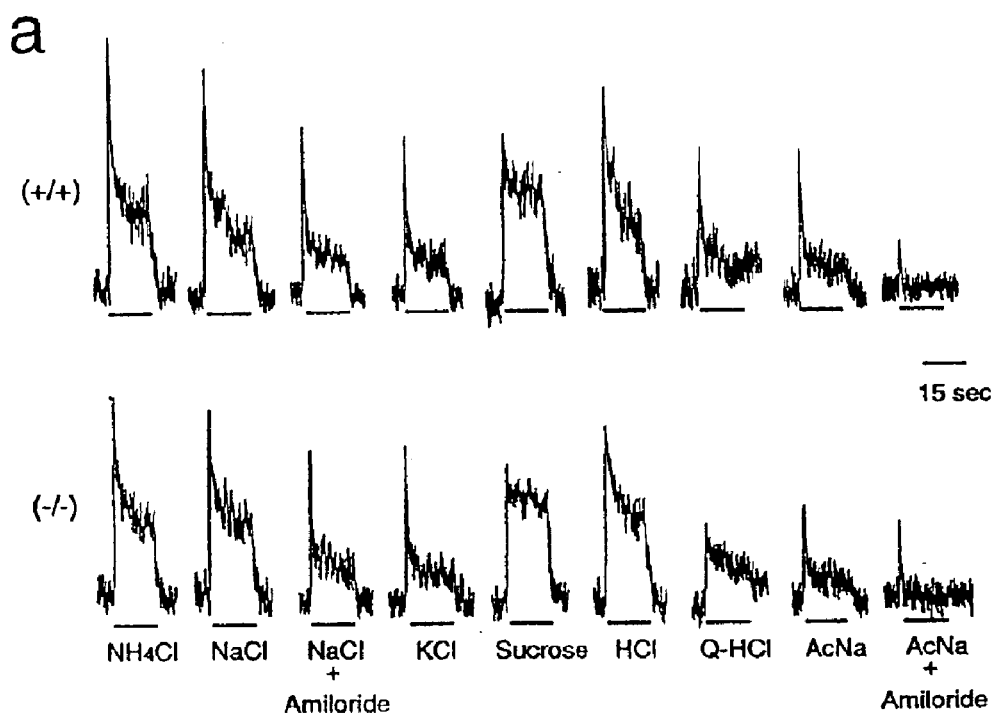
FIG. 6 is a view showing the result of responses to various tastant stimuli in the chorda tympani nerve of $Na_v2$ knockout mice of the present invention.
Figure 6:
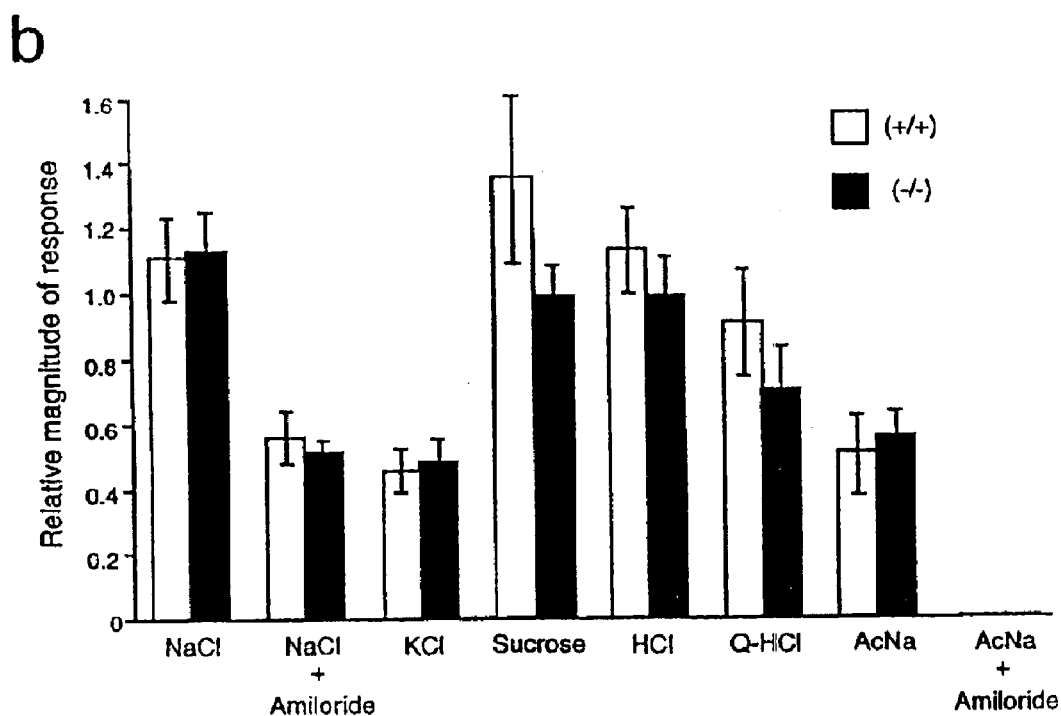

The taste solutions were 0.1 M $NH_4Cl$, 0.1 M NaCl, 0.5 M sucrose, 0.01 M HCl, 0.02 M Q-HCl, 0.1 M KCl and 0.1 M $CH_3COONa$ (AcNa). These solutions were made up with distilled water and 0.1 mM amiloride solution. Each solution and rinsing water were applied to the anterior part of the tongue at room temperature (25±2° C.). The tongue was rinsed for at least 45 sec between successive stimuli. The magnitude of the whole nerve response was measured as the height of the integrated response from the baseline at 10 sec after onset of stimulation. Recorded results of the chorda tympani response to various taste stimuli are shown in FIG. 6a. The magnitudes of the responses to various taste stimuli expressed as relative values with the magnitude of the response of 0.1 M $NH_4Cl$ taken as the standard are shown in FIG. 6b.

The neurophysiological responses to 0.02 M Q-HCl, and 0.1 M $CH_3COONa$ were of similar intensity between the null-mutant and wild-type mice. Responses to 0.1 M NaCl and 0.1 M $CH_3COONa$ were decreased to the same degree by amiloride application in both groups of mice, indicating that amiloride-sensitive channels in taste buds in the mutant mice function normally. Similar results were observed in the null-mutant and wild-type mice under the acute salt appetite condition. This finding together with the normal behavioral response to various tastants under water- and salt-sufficient conditions (FIG. 5) shows that the taste reception of the null mutants is not impaired.

Figure 7:
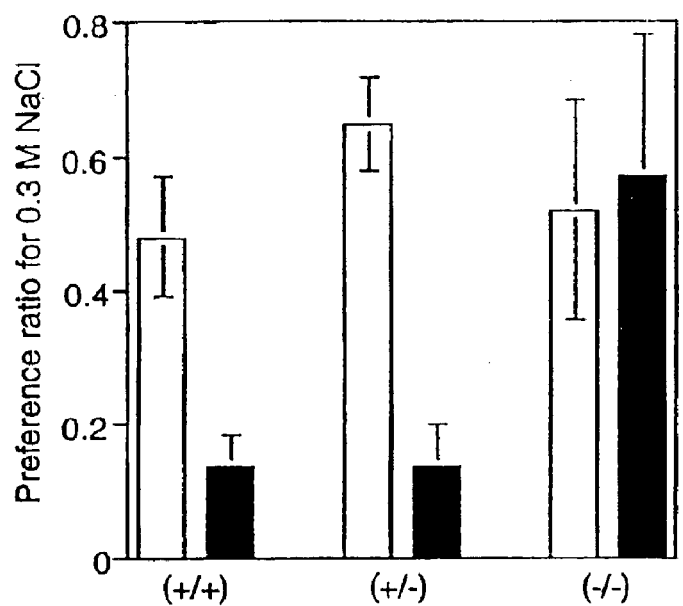
FIG. 7 is a view showing the result of the measurement of preference ratio for 0.3 M NaCl solution and total fluid intake of $Na_v2$ knockout mice of the present invention before and after 24-h dehydration.
Figure 7:
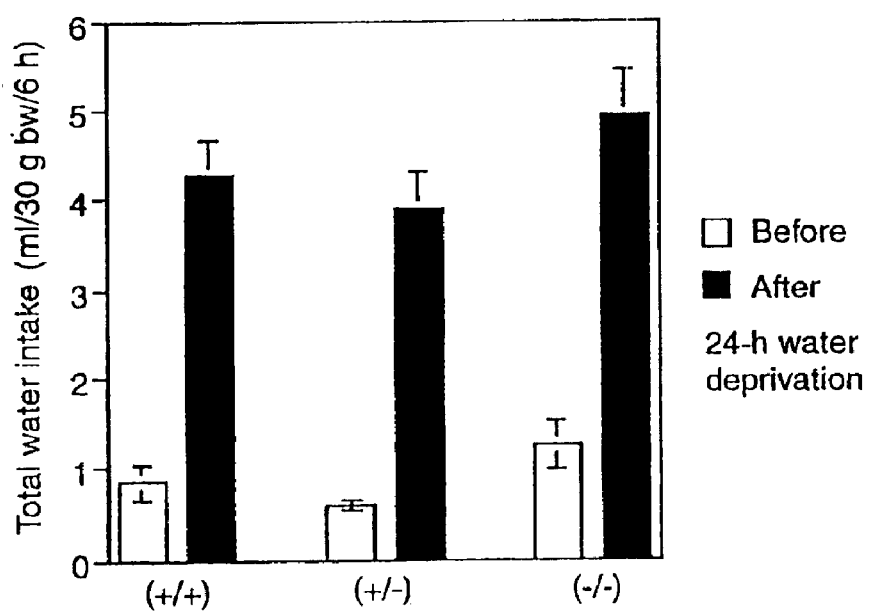

Under the water-depleted condition, animals take in a large quantity of water and avoid hypertonic saline to recover from the hypertonic state. The preference to hypertonic saline (0.3 m NaCl) before and after 24-h dehydration was examined. Before testing, mice were trained to drink water from two bottles for one week. On the day before dehydration, mice were presented with a choice between water and 0.3 M NaCl at 10.00 h, and then measured for fluid intake at 16.00 h. At 10.00 h on the next day, the bottles were removed. Dry food was placed throughout the period of water deprivation. After 24-h dehydration, the two bottles were returned and fluid intakes were measured at 16.00 h. The results are shown in FIG. 7. The null mutants showed an abnormal ingestion of hypertonic saline under the water-depleted condition. Preference ratio for 0.3 M NaCl solution (FIG. 7a) and total fluid intake (FIG. 7b) were measured before and after 24-h dehydration. In this experiment, n=6 (+/+), 6(+/−) and 6(−/−). Vertical bars in the FIG. 7 indicate S.E., and the asterisk shows that a significant difference (P<0.05) between $Na_v2^{-/-}$ and $Na_v2^{+/+}$ mice were observed. In contrast to the wild-type and heterozygous mutant mice, which showed markedly decreased preference ratios to hypertonic saline after dehydration, the null mutants showed no change in the preference ratio (FIG. 7a). Total water intake (water plus 0.3 M NaCl) did not differ among the groups both before and after 24-h dehydration. The total water intake of all the groups showed more than a four-fold increase after dehydration (FIG. 7b).

Blood was recovered from animals before or after dehydration by decapitation, and then the concentrations of plasma electrolytes were measured by using an electrolyte analyzer (9180, AVL Scientific, GA). The electrolyte concentrations in the serum before and after dehydration were normal in both wild-type and homozygous mutant mice (n=6 each). The electrolyte concentrations in wild-type and homozygous mutant mice before dehydration are as follows respectively: 153.6±0.6 and 153.0±1.2 mM for $Na^+$; 4.6±0.1 and 4.7±0.1 mM for $K^+$; 118.5±0.6 and 118.3±0.9 mM for $Cl^-$. The electrolyte concentrations in wild-type and homozygous mutant mice after dehydration are as follows respectively: 151.6±0.8 and 150±0.3 mM for $Na^+$; 6.5±0.2 and 6.7±0.2 mM for $K^+$; 116.0±1.0 and 116.4±0.8 mM for Cl⁻. This suggests that the null mutants immediately excreted excessive amounts of sodium into urine, and thus the renal function of null mutants works normally.

Furthermore, motivated salt appetite was induced by intraperitoneal injection of a diuretic drug, furosemide, and sodium-depleted food, then the sodium-depletion induced salt appetite test was carried out in the following way. Before testing, control measurements of water and 0.3 M NaCl intake were performed for several days. At 10.00 h, mice were injected intraperitoneally with 0.12 ml of normal saline (0.9% NaCl). The bottle of 0.3 M NaCl was withdrawn and sodium-depleted food was supplied in place of a normal diet. The second injection of normal saline was given at 16.00 h. On the following day, water and 0.3 M NaCl were presented at 10.00 h and intakes of 0.3 M NaCl and water were measured at 12.00, 14.00 and 16.00 h. After that, a similar protocol with furosemide injection (0.6 mg in 0.12 ml of normal saline) was performed with sodium-depleted food in the same mice (acute salt-appetite condition). Finally, the same protocol, except that normal sodium-containing food was supplied, was performed to evaluate the effect of sodium-depleted food. The results are shown in FIG. 8.

Figure 8:
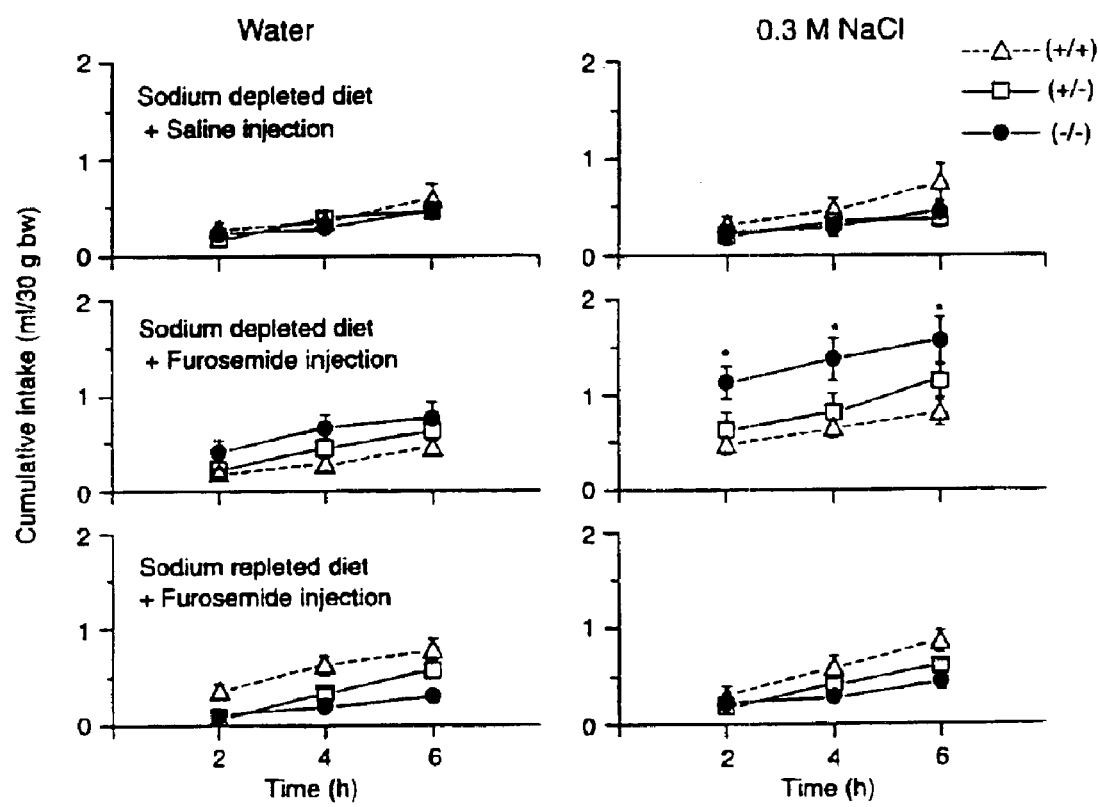
FIG. 8 is a view showing the result of the sodium-depletion induced salt appetite test for $Na_v2$ knockout mice of the present invention.

The ingested volumes of water and 0.3 M NaCl are shown in FIG. 8 in cumulative values for every 2 h. The results of the behavioral study are shown in FIG. 8 as plotted mean cumulative intakes of 0.3 M NaCl (right) and water (left) per 2 h starting just after each experimental procedure as follows: a sodium-depleted diet combined with normal saline injection (top), a sodium-depleted diet combined with furosemide injection (middle), and a sodium-contained diet combined with furosemide injection (bottom). In this experiment, n=10 (+/+), 10 (+/−) and 10 (−/−). Vertical bars in FIG. 8 indicate S. E., and the asterisk shows that a significant difference ($P<0.05$) between $Na_v2^{-/-}$ and $Na_v2^{+/+}$ mice were observed. As shown in FIG. 8, under the control condition in which isotonic saline was injected in place of a furosemide solution, the ingested volumes of water and 0.3 M NaCl were comparable among the three groups (graphs at the top). Under the acute salt appetite condition induced by furosemide injection with a sodium-depleted diet, however, the null-mutants showed an approximately two-fold increase in the ingestion of 0.3 M NaCl compared with the wild-type and heterozygous mutant mice (right graph at the middle). This abnormal ingestion of hypertonic saline stopped when sodium-containing food was provided (graph at the bottom).

[$Na_v2$ Channel is a Sodium Concentration-dependent Sodium Channel]

It has been verified that $Na_v2$ channel is a sodium concentration-dependent sodium channel by following experiments.

First, an anti-$Na_v2$ antibody was constructed as follows: a peptide comprised of an amino acid sequence (SVSETVPIASGESDIK; Seq. ID No. 8), which exists in inter domain 2-3 of rat $Na_v2$ channel, was combined to hemocyanin, then a white rabbit was immunized with the hemocyanin-combined peptide as an immunogen, and anti-rat $Na_v2$ rabbit antiserum was constructed by a usual method. The constructed antiserum was purified by a column in which the peptide used as the immunogen was fixed, and an anti-$Na_v2$ antibody was obtained. The specificity of the anti-$Na_v2$ antibody was confirmed by Western blot and immunohistochemical analysis. When the purified anti-$Na_v2$ antibody was used, no non-specific positive signal was observed in sections of brain, lung, dorsal root ganglia and tongue prepared from gene-deficient mice.

Next, nerve cells in dorsal root ganglia were isolated. The dorsal root ganglia were prepared from wild-type and $Na_v2$ gene-deficient mice of 8–16 weeks of age. Nerve cells were dispersedly isolated from the dorsal root ganglia according to the method of Renganathan et al. (J Neurophysiol 84, 710–718, 2000). Before used for an ion imaging experiment, the dispersedly isolated nerve cells were cultured under the condition of the humidity of 100% and the temperature of 37° C., and with 5% of carbon dioxide, then adhered to the glass of culture plates. All nerve cells were confirmed to be $Na_v2$-positive by staining nerve cells of dorsal root ganglia derived from wild-type mice with the above-mentioned anti-$Na_v2$ antibody. The size of the dispersedly isolated nerve cells were comprised of 3 groups of small (25 micron or smaller in diameter: about 50%), medium (25 to 40 micron in diameter: about 40%), and large (40 micron or larger in diameter: about 10%). However, there was no difference between the materials isolated from wild-type and gene-deficient mice in the size, shape and survival rate of these 3 types of cell. The survival rate was verified by Tripan blue staining.

In addition, nerve cells of subformical organs were also isolated. The subformical organs were prepared from wild-type and $Na_v2$ gene-deficient mice of 8–16 weeks of age. In order to visualize the subformical organs, Evans blue was intraperitoneally injected in advance. The subformical organs were dispersed according to the method of Jurzak et al. (Brain Res 662, 198–208, 1994). As in the case of nerve cells of dorsal root ganglia, the dispersedly isolated nerve cells were cultured under the condition of the humidity of 100% and the temperature of 37° C., and with 5% of carbon dioxide, then adhered to the glass of culture plates, and then used for the experiment. Some nerve cells of subformical organs derived from wild-type mice were stained with the above-mentioned anti-$Na_v2$ antibody, and a ratio of $Na_v2$-positive nerve cells was about 20 to 30%. There was no difference between the nerve cells isolated from wild-type and gene-deficient mice in the size and survival rate.

With regard to the nerve cells of dorsal root ganglia or subformical organs prepared from the above-mentioned wild-type and $Na_v2$ gene-deficient mice, intracellular sodium ion and intracellular calcium ion were measured. SBFI/AM (sodium-binding benzofuran isophthalate acetoxymethyl ester) was used for measuring intracellular sodium ion, and Fura-2/AM was used for measuring intracellular calcium ion. Cultured cells loaded with these indicators were adhered to culture plates, and the culture plates were fixed to the stage of a microscope. Fluorescence ratio (F340/F380) was monitored by the fluorescence imaging system. In order to measure data, samplings were conducted every 10 seconds for the nerve cells of dorsal root ganglia, and every 20 seconds for those of subformical organs respectively. Before the measurement, the nerve cells were incubated with physiological isotonic liquid (145 mM of extracellular sodium concentration) for 30 to 60 minutes, and while measuring, the nerve cells were exposed to a certain perfusate (5 mM of KCl, 2.5 mM of $CaCl_2$, 1 mM of $MgCl_2$, 10 mM of HEPES, 10 mM of NaOH, NaCl at the prescribed concentration, pH 7.4, (neutralization by HCl), and the perfusate (extracellular liquid) was perfused at a certain speed (1 ml/min) at room temperature.

Figure 9:
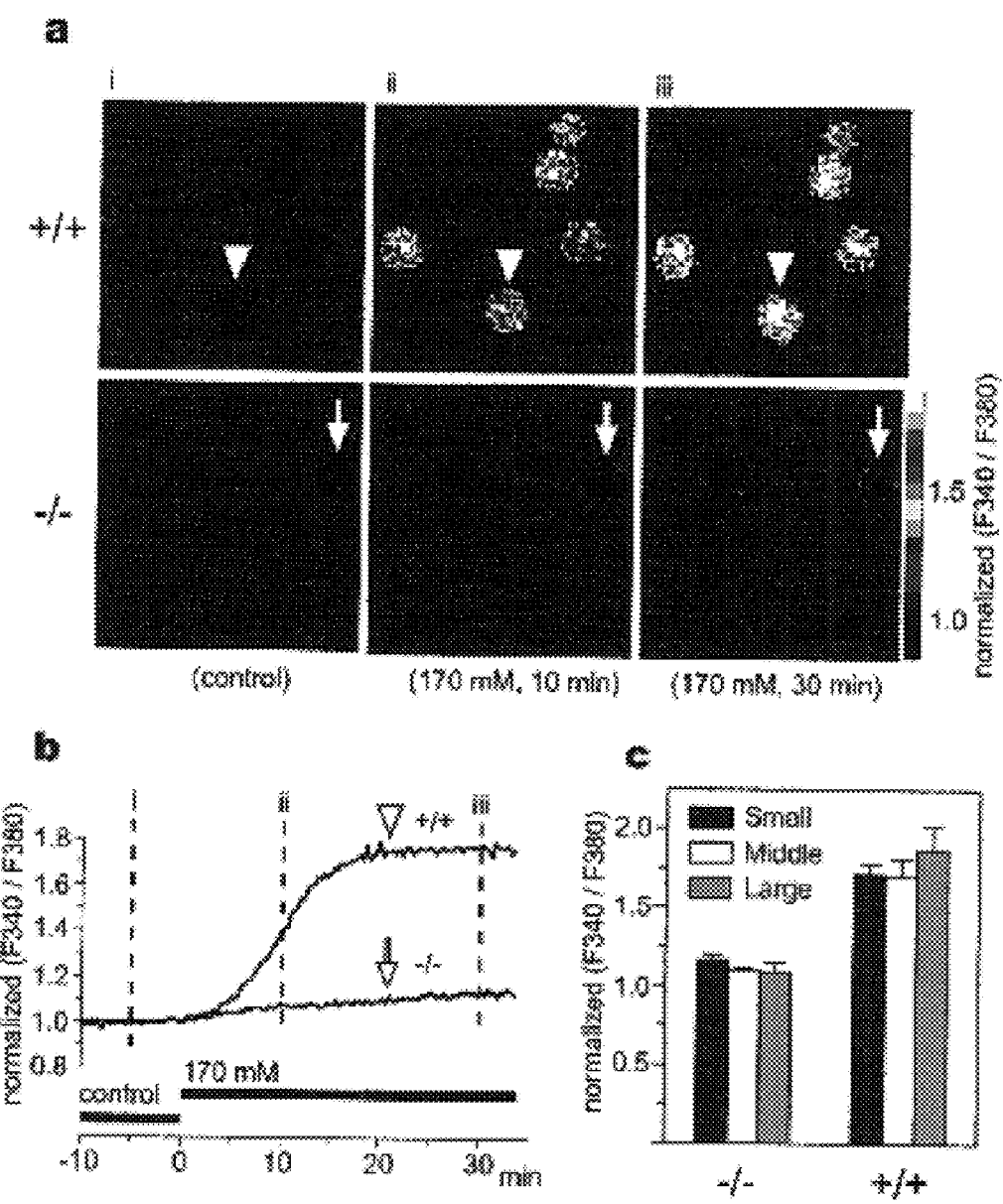
FIG. 9 is a view showing the result of the fluorescence imaging of fluorescence ratio (F340/F380) of intracellular sodium ion and extracellular calcium ion in nerve cells of dorsal root ganglia prepared from wild-type mice and Nav2 gene-deficient mice.
Figure 10:
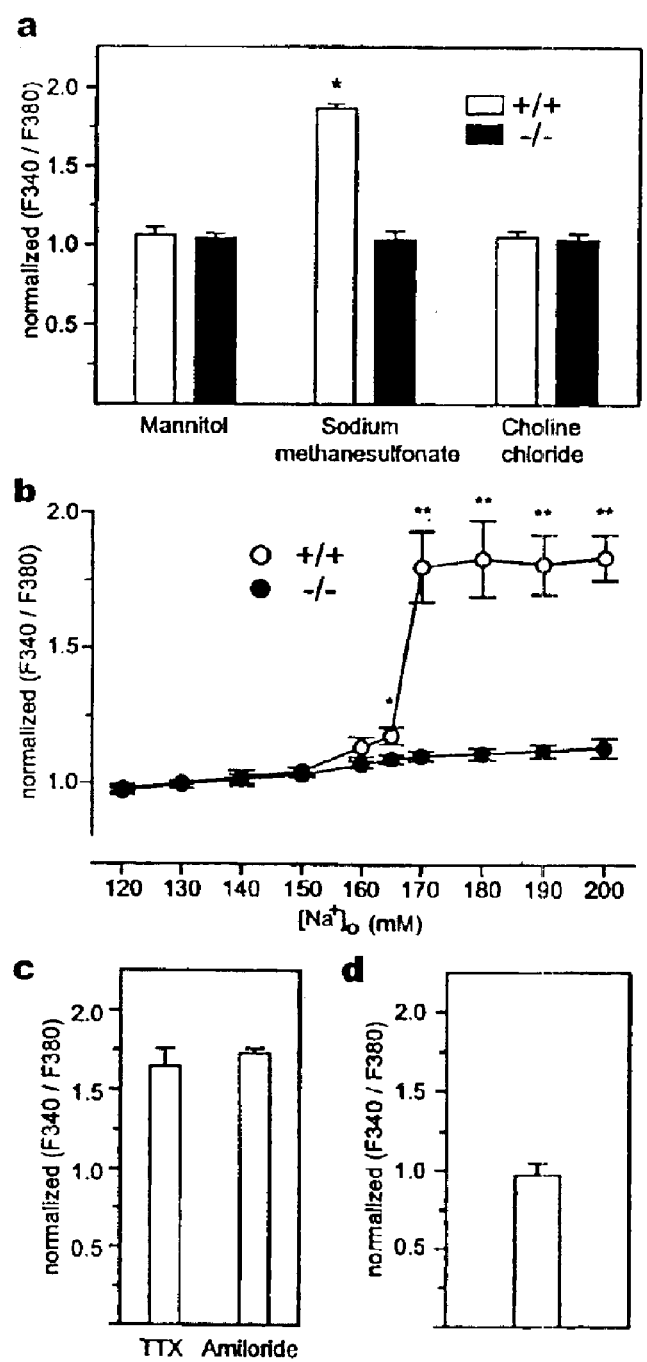
FIG. 10 is a view showing the result of the fluorescence imaging of fluorescence ratio (F 340/F380) of intracellular sodium ion and extracellular calcium ion in nerve cells of dorsal root ganglia prepared from wild-type mice and Nav2 gene-deficient mice.

The results of the fluorescence imaging of fluorescence ratio (F340/F380) in nerve cells of dorsal root ganglia are shown in FIG. 9 and FIG. 10. As shown in FIG. 9, when the concentration of the extracellular NaCl was increased to 145 to 170 mM, the concentration of intracellular sodium ion in nerve cells of dorsal root ganglia derived from wild-type mice showed a rapid increase, and reached to steady state straightly. On the other hand, in the nerve cells of dorsal root ganglia derived from gene-deficient mice, an increase of the intracellular sodium ion concentration, such as observed in wild-type mice, was not observed at all (FIGS. 9a and 9b). Further, the increase of sodium in the nerve cells of dorsal root ganglia derived from wild-type mice was observed in nerve cells of every size (FIG. 9c). This is consistent with the fact that $Na_v2$ expresses in every nerve cells of dorsal root ganglia of wild-type mice.

In addition, as shown in FIG. 10, the increase of the intracellular sodium ion concentration was caused not by osmotic pressure stimulus using mannitol or by single stimulus of chlorine ions using choline chloride, but by single stimulus of sodium ions using sodium methanesulfonate (FIG. 10a). Accordingly, it has been found that this phenomenon is caused only by the increase of sodium ion concentration. When the extracellular sodium concentrations were arranged to be 120, 130, 140, 150, 160, 165, 170, 180, 190 and 200 mM, 10 concentrations in all, with sodium chloride and the changes in intracellular sodium ion concentration were analyzed, there was no response in the range of 120 to 150 mM, the increase was observed in the extracellular sodium ion concentration of 160 and 165 mM, and extremely significant increase was observed in the extracellular sodium ion concentration of 170 mM and higher (FIG. 10b). In case the extracellular sodium was rearranged to the original concentration of 145 mM at that time, it was observed that the intracellular sodium concentration gradually changed to the original concentration. As there was no intracellular sodium store, it was concluded that this increase of the intracellular sodium concentration was attributed to an influx from extracellular regions via $Na_v2$ channel. The threshold value of the channel opening is presumed to be in the range of 160 to 170 mM.

In order to investigate the possibility that molecules other than $Na_v2$ channel are involved in the influx of sodium into the cells accompanied with this increase of the extracellular sodium ion concentration, the effects of each blocker of various sodium ion pumps, sodium ion transporters, sodium ion channels were examined. As a result, it was found that there was no influence of TTX-sensitive voltage-dependent sodium channels (FIG. 10c), amiloride-sensitive sodium channels (FIG. 10c), sodium glucose co-transporters, sodium calcium antiporters, sodium potassium chloride transporters and sodium potassium pumps. Further, it was concluded that TTX-nonsensitive voltage-dependent sodium channels were not involved in this phenomenon observed in cell types of every size because they expressed specifically in small nerve cells of dorsal root ganglia. The fact that sodium calcium antiporters were not involved in this phenomenon was also confirmed by calcium imaging (FIG. 10d).

Figure 11:
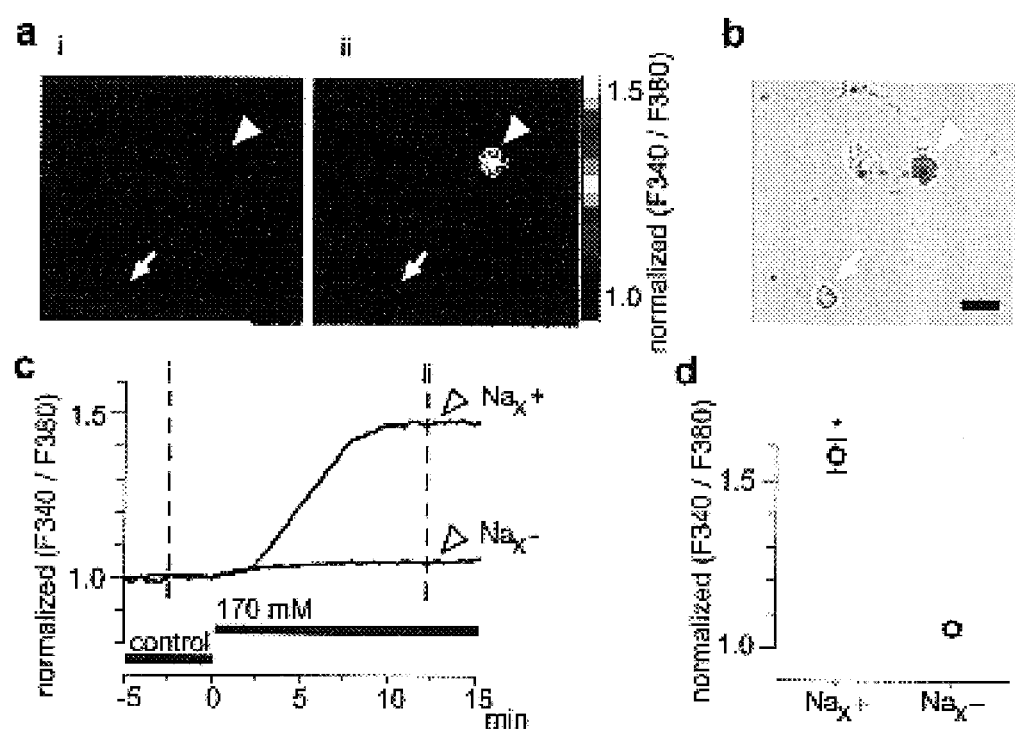
FIG. 11 is a view showing the result of the fluorescence imaging of fluorescence ratio (F340/F380) of intracellular sodium ion and extracellular calcium ion in nerve cells of subfomical organs prepared from wild-type mice and Nav2 gene-deficient mice.

The results of the fluorescence imaging of fluorescence ratio (F340/F380) in nerve cells of subformical organs are shown in FIG. 11. As shown in FIG. 11, basically same results as in the case of the nerve cells of dorsal root ganglia are obtained also in the nerve cells of subformical organs, which are organs for detecting sodium ion concentration in the central nervous system. About 20 to 30% of the nerve cells of subformical organs were $Na_v2$ immuno-positive cells, and an increase of the intracellular sodium ion concentration was observed in these $Na_v2$ immuno-positive cells, however, no increase of the intracellular sodium ion concentration was observed in $Na_v2$ immuno-negative cells, as in the case of $Na_v2$ gene-deficient mice. These results verify that $Na_v2$ is a sodium channel which makes sodium ion flow into cells in an extracellular sodium ion concentration-dependent manner in subformical organs as well. In other words, it has been found that $Na_v2$ is a new sodium channel of a sodium concentration-dependent sodium channel.

INDUSTRIAL APPLICABILITY

A null mutant non-human animal characterized in showing salt intake behavior similar to that of wild-type animals under water-sufficient conditions and showing much more intakes of hypertonic saline compared with wild-type animals under water- and salt-depleted conditions, for example, an $Na_v2$ channel gene-deficient mouse, is useful as a model animal of excessive salt intake experiments. By using this $Na_v2$ channel gene-deficient mouse, it has been revealed that $Na_v2$ channel acts a role to sense and control sodium ion level in cerebrospinal fluid, and that $Na_v2$ channel expresses in neurons and ependymal cells in restricted areas of the central nervous system, particularly in the circumventricular organs which are involved in body-fluid homeostasis, and that $Na_v2$ channel plays an important role in the central sensing of body-fluid sodium level and regulation of salt intake behavior.

What is claimed is:

1. A null mutant mouse comprising a homozygous disruption in the endogenous genes that code for $Na_v2$, wherein the disruption results in the lack of $Na_v2$ protein expression, and wherein the mouse shows salt intake behavior similar to that of a wild-type mouse under water-sufficient conditions and shows an increase of intake of hypertonic saline compared with a wild-type mouse under water-depleted conditions.

2. A method of screening a material that affects the function or expression of the $Na_v2$ protein comprising the steps of:

1) administering a material to a null mutant mouse comprising a homozygous disruption in the endogenous genes that code for $Na_v2$, wherein the disruption results in the lack of $Na_v2$ protein expression, and wherein the mouse shows salt intake behavior similar to that of a wild-type mouse under water-sufficient conditions and shows an increase of intake of hypertonic saline compared with a wild-type mouse under water-depleted conditions;

2) measuring the intake of hypertonic saline under water-sufficient and water-depleted conditions; and 3) comparing said measurement to the intake of a wild-type mouse under said conditions, wherein a difference between the wild-type mouse and the null mutant mouse shows an effect on the function or expression of the $Na_v2$ protein.

* * * * *

SEQUENCE LISTING

```
<160> NUMBER OF SEQ ID NOS: 8

<210> SEQ ID NO 1
<211> LENGTH: 446
<212> TYPE: DNA
<213> ORGANISM: Rattus norvegicus

<400> SEQUENCE: 1
atgttgactt ccccagagcc gaagggcctt gtcccattca cggcagagtc acttgaactt      60
ataaaaaatc acattgctaa aaaatgcaac gaagagcatg aagaagaaga tttaaaacca     120
agccgggata tagaagcagg caaaaaactt ccatttgcct atggaaccct tcctcaagga     180
accgtgtcag agcccttgga agatgtggat ccatactact atgttaagag aaatactttc     240
atggtcttaa acagaaacag agtcatcttc aggttcaatg cggtttccat cctctgcacg     300
ttgtctcctt taagctctct cagaagagct gttatcaagg ttttggtgca ccccctttg     360
```

```
cgcctgctga ttttaattag tgttctcacc gacagcatac ttatgtgcat gagtaaccta    420
ccggaatgga tattggcagt agagaa                                         446

<210> SEQ ID NO 2
<211> LENGTH: 5482
<212> TYPE: DNA
<213> ORGANISM: Mus musculus
<220> FEATURE:
<221> NAME/KEY: CDS
<222> LOCATION: (252)..(5297)

<400> SEQUENCE: 2
cacgcgtcga ctagtacggg ggggggggag gggttggtct gtaggtggtc tctgggtctg     60
tggagctagc ctggtggctg agtgtttagc tggaagcagc agtggaccgc aaccacattg    120
caacaacctc cgtagtagag atctgagaag acaagcccag gagagcaaag ggctctcgtg    180
agccttgcat ctggggttct tgctggagtt ttagtgaaga ctagcatttg acagcaacta    240
taaaaccgaa a atg ttg act tcc cca gag ccg aag ggc ctt gtc cca ttt    290
            Met Leu Thr Ser Pro Glu Pro Lys Gly Leu Val Pro Phe
              1               5                  10 aca aca gag tca ctt gaa ctt ata gaa aat cac att gct aaa aaa tgc    338
Thr Thr Glu Ser Leu Glu Leu Ile Glu Asn His Ile Ala Lys Lys Cys
         15                  20                  25 aat gaa gac ccc gaa gaa gaa gaa ggt tta aaa cca agt cgt aat cta    386
Asn Glu Asp Pro Glu Glu Glu Glu Gly Leu Lys Pro Ser Arg Asn Leu
 30                  35                  40                  45 gaa gct ggc aaa aga ctt cca att ccc tat gga acc ctc cct cga gga    434
Glu Ala Gly Lys Arg Leu Pro Ile Pro Tyr Gly Thr Leu Pro Arg Gly
                 50                  55                  60 acc gtg tca gag ccc ttg gaa gat gtg gat cca tac tac tat gtt aag    482
Thr Val Ser Glu Pro Leu Glu Asp Val Asp Pro Tyr Tyr Tyr Val Lys
             65                  70                  75 aga aat act ttc atg gtc tta aac aga agc aga gtc atc ttc agg ttc    530
Arg Asn Thr Phe Met Val Leu Asn Arg Ser Arg Val Ile Phe Arg Phe
         80                  85                  90 aat gcg gtt tcc atc ttc tgc aca ttg tct cct cta aac tcc ctc aga    578
Asn Ala Val Ser Ile Phe Cys Thr Leu Ser Pro Leu Asn Ser Leu Arg
 95                 100                 105 aga gca gct atc aag gct ttg gtg cat ccc ctt ttt cgc ctg ctg att    626
Arg Ala Ala Ile Lys Ala Leu Val His Pro Leu Phe Arg Leu Leu Ile
110                 115                 120                 125 tta atc agc gtt ctc act gac agc ata ctt atg tgc atg agt aat cta    674
Leu Ile Ser Val Leu Thr Asp Ser Ile Leu Met Cys Met Ser Asn Leu
                130                 135                 140 cca gaa tgg ata ttg gca ata gag aat act ttg ctt ggg att tac gca    722
Pro Glu Trp Ile Leu Ala Ile Glu Asn Thr Leu Leu Gly Ile Tyr Ala
            145                 150                 155 ttt gaa ata ctt gta aaa gtc att gca aga ggt atc tgg gca ggt tca    770
Phe Glu Ile Leu Val Lys Val Ile Ala Arg Gly Ile Trp Ala Gly Ser
                160                 165                 170 ttt tcc ttc ctt ggg gat ctt tgg aac tgg ctt gat ttc agt gta act    818
Phe Ser Phe Leu Gly Asp Leu Trp Asn Trp Leu Asp Phe Ser Val Thr
            175                 180                 185 ttg ttc gag cta atc aca agg ttt tca cct cta agc tcc ttt tta atg    866
Leu Phe Glu Leu Ile Thr Arg Phe Ser Pro Leu Ser Ser Phe Leu Met
190                 195                 200                 205 ctt aaa act atc aga act ttc cga att ttg aag att atc cct ttg aac    914
Leu Lys Thr Ile Arg Thr Phe Arg Ile Leu Lys Ile Ile Pro Leu Asn
                210                 215                 220
```

```
                                            -continued cac ggc ctg cag tct att gtg atg aca ctg gcc cag tgt ttg aag aaa        962
His Gly Leu Gln Ser Ile Val Met Thr Leu Ala Gln Cys Leu Lys Lys
            225                 230                 235 cta ttt ggt gcc att gcc cta gct ctg ttt ttt ctg gct gtg ttt tca       1010
Leu Phe Gly Ala Ile Ala Leu Ala Leu Phe Phe Leu Ala Val Phe Ser
        240                 245                 250 cta ctt gga atg ggc ctc ttc atg ggc aac ctg aag cac aaa tgt ctg       1058
Leu Leu Gly Met Gly Leu Phe Met Gly Asn Leu Lys His Lys Cys Leu
    255                 260                 265 cgg tgg cca gaa gaa aat gaa aat gaa acg ctg cac aac aga act gga       1106
Arg Trp Pro Glu Glu Asn Glu Asn Glu Thr Leu His Asn Arg Thr Gly
270                 275                 280                 285 agc ctt aac tat agt cca gaa aga ata aac ttc tac tac atg gaa gga       1154
Ser Leu Asn Tyr Ser Pro Glu Arg Ile Asn Phe Tyr Tyr Met Glu Gly
                290                 295                 300 gcg aaa tat gct ctc ctt tgc ggc aac agg aca gat gct ggc cag tgt       1202
Ala Lys Tyr Ala Leu Leu Cys Gly Asn Arg Thr Asp Ala Gly Gln Cys
            305                 310                 315 ccg gaa ggt tat gtg tgt gta aaa gaa ggc aca aat cct gac aat ggc       1250
Pro Glu Gly Tyr Val Cys Val Lys Glu Gly Thr Asn Pro Asp Asn Gly
        320                 325                 330 ttc aca agt ttt gac aac ttt ggc tgg tcc ctt ctt gct atg ttt cga       1298
Phe Thr Ser Phe Asp Asn Phe Gly Trp Ser Leu Leu Ala Met Phe Arg
    335                 340                 345 ttg atg aca cag gat tac cct gaa tta ctt tat cac cag atc ctt tat       1346
Leu Met Thr Gln Asp Tyr Pro Glu Leu Leu Tyr His Gln Ile Leu Tyr
350                 355                 360                 365 gct tca gga aag gtc tac atg ata ttt ttt gtt atg atc agt ttc tgg       1394
Ala Ser Gly Lys Val Tyr Met Ile Phe Phe Val Met Ile Ser Phe Trp
                370                 375                 380 ttt gcc ttc tat ttg aca agt ttg ttc ttg ggc ata ctc act atg acc       1442
Phe Ala Phe Tyr Leu Thr Ser Leu Phe Leu Gly Ile Leu Thr Met Thr
            385                 390                 395 tat gaa aag gaa aag cag aga gcc tgt gag gaa tct gga ggc ctt gat       1490
Tyr Glu Lys Glu Lys Gln Arg Ala Cys Glu Glu Ser Gly Gly Leu Asp
        400                 405                 410 ccc aaa tgt caa cag aca gtg aaa gaa ctc gac gaa gaa aat gac gca       1538
Pro Lys Cys Gln Gln Thr Val Lys Glu Leu Asp Glu Glu Asn Asp Ala
    415                 420                 425 gct gag atg gaa act aca caa ata gaa atg aag aaa aga tcc cca act       1586
Ala Glu Met Glu Thr Thr Gln Ile Glu Met Lys Lys Arg Ser Pro Thr
430                 435                 440                 445 tct ata aac acc aca ctg gat ata ctg gaa gac act acc ctc gga cac       1634
Ser Ile Asn Thr Thr Leu Asp Ile Leu Glu Asp Thr Thr Leu Gly His
                450                 455                 460 aga gaa gaa cca gaa aca tcc agg aag aaa tgc cca ata tgt tgg cat       1682
Arg Glu Glu Pro Glu Thr Ser Arg Lys Lys Cys Pro Ile Cys Trp His
            465                 470                 475 aag ttt att aaa acc tgc ttc atc tgg aaa tgc tct ccc tgt tgg gta       1730
Lys Phe Ile Lys Thr Cys Phe Ile Trp Lys Cys Ser Pro Cys Trp Val
        480                 485                 490 aaa ctg aac gag ttt gct gat aga gtt ata aca cac cca ttg gct gat       1778
Lys Leu Asn Glu Phe Ala Asp Arg Val Ile Thr His Pro Leu Ala Asp
    495                 500                 505 ctt ttt ctt gtc atc tgc atc gtt tta aac ata tgc ttc ctc gcc cta       1826
Leu Phe Leu Val Ile Cys Ile Val Leu Asn Ile Cys Phe Leu Ala Leu
510                 515                 520                 525 gaa cat ttt cca atg agc gag gag ctc agg tct ctc ctt cac gtt gga       1874
Glu His Phe Pro Met Ser Glu Glu Leu Arg Ser Leu Leu His Val Gly
```

| | | | |
|---|---|---|---|
| aat ttg gtt ttt att gga att tac aca ata gaa ctg att ttg aag ata<br>Asn Leu Val Phe Ile Gly Ile Tyr Thr Ile Glu Leu Ile Leu Lys Ile<br>545 550 555 | 1922 |
| atc gct atg cat cca tat ggg tat ttt caa ata agc tgg aat att ttt<br>Ile Ala Met His Pro Tyr Gly Tyr Phe Gln Ile Ser Trp Asn Ile Phe<br>560 565 570 | 1970 |
| gac agt ata ctt gtg gtt ttg gag tta aca gaa att tta cta gca gat<br>Asp Ser Ile Leu Val Val Leu Glu Leu Thr Glu Ile Leu Leu Ala Asp<br>575 580 585 | 2018 |
| gtt gaa gga cta gct gtt tta ata aca gtc cca ttg ata ttt ata aaa<br>Val Glu Gly Leu Ala Val Leu Ile Thr Val Pro Leu Ile Phe Ile Lys<br>590 595 600 605 | 2066 |
| ctg ggg aag tac gga cca cca ttt aag agt ttg atg cgc atc ctt ggt<br>Leu Gly Lys Tyr Gly Pro Pro Phe Lys Ser Leu Met Arg Ile Leu Gly<br>610 615 620 | 2114 |
| agc tca ttg atg gcc ctg aaa gat ttg gtc ctg ttg ctc tgc ata ttc<br>Ser Ser Leu Met Ala Leu Lys Asp Leu Val Leu Leu Leu Cys Ile Phe<br>625 630 635 | 2162 |
| gtt tac ttc tct gct gtg ttc ggc atg aag ctg ttt ggt cga agt tac<br>Val Tyr Phe Ser Ala Val Phe Gly Met Lys Leu Phe Gly Arg Ser Tyr<br>640 645 650 | 2210 |
| aag gat tgt gtc tgc cac ata aag gaa gac tgc caa ccc caa cgc tgg<br>Lys Asp Cys Val Cys His Ile Lys Glu Asp Cys Gln Pro Gln Arg Trp<br>655 660 665 | 2258 |
| cac atg agt gac ttc ctt cat gcc tac atg acc gtg ttc cga atc ctc<br>His Met Ser Asp Phe Leu His Ala Tyr Met Thr Val Phe Arg Ile Leu<br>670 675 680 685 | 2306 |
| tgt gga gag tgg ata gag aca tta tgg gag tgt atg gag gtt gca ggc<br>Cys Gly Glu Trp Ile Glu Thr Leu Trp Glu Cys Met Glu Val Ala Gly<br>690 695 700 | 2354 |
| cag gcc tgg tgt att cct ttt tac atg atg gtc att tta att gga aac<br>Gln Ala Trp Cys Ile Pro Phe Tyr Met Met Val Ile Leu Ile Gly Asn<br>705 710 715 | 2402 |
| tta ttg ata ctt tac ctc ttt gtg aca ttg gtg agc tct ttc agt tac<br>Leu Leu Ile Leu Tyr Leu Phe Val Thr Leu Val Ser Ser Phe Ser Tyr<br>720 725 730 | 2450 |
| tat gat gct aca tcg gaa gtg aac aaa gaa gcc aaa aac ctt cag ctt<br>Tyr Asp Ala Thr Ser Glu Val Asn Lys Glu Ala Lys Asn Leu Gln Leu<br>735 740 745 | 2498 |
| gcc atg gca agg ata aag tcg gga ata aac tcc atg ctt ctt aaa tta<br>Ala Met Ala Arg Ile Lys Ser Gly Ile Asn Ser Met Leu Leu Lys Leu<br>750 755 760 765 | 2546 |
| atg tgc aca gaa aga agt gtt cct aca gaa gca aca gac caa ata tgt<br>Met Cys Thr Glu Arg Ser Val Pro Thr Glu Ala Thr Asp Gln Ile Cys<br>770 775 780 | 2594 |
| gat cca agt gtt aaa gag aat att tct ggc cat act ctt tct gaa ctg<br>Asp Pro Ser Val Lys Glu Asn Ile Ser Gly His Thr Leu Ser Glu Leu<br>785 790 795 | 2642 |
| agc aac acc caa act ttc ctc aga tat aag gac cag agc agc agc act<br>Ser Asn Thr Gln Thr Phe Leu Arg Tyr Lys Asp Gln Ser Ser Ser Thr<br>800 805 810 | 2690 |
| gag aaa act cca gtg act gaa tct gag agt caa tct ctg att gct agt<br>Glu Lys Thr Pro Val Thr Glu Ser Glu Ser Gln Ser Leu Ile Ala Ser<br>815 820 825 | 2738 |
| ccc agt gcc tct gaa act gtg ccg att gct tca gga gaa tct gat ata<br>Pro Ser Ala Ser Glu Thr Val Pro Ile Ala Ser Gly Glu Ser Asp Ile<br>830 835 840 845 | 2786 |
| gaa aat ctg gat aac aag gag act cgg agc aag tct ggg aat gga ggc<br> | 2834 |

```
Glu Asn Leu Asp Asn Lys Glu Thr Arg Ser Lys Ser Gly Asn Gly Gly
                850                 855                 860 agt aaa gag aaa atg aag cag tct agc tca tct gag tgc agc aca gtt        2882
Ser Lys Glu Lys Met Lys Gln Ser Ser Ser Ser Glu Cys Ser Thr Val
        865                 870                 875 gat atc gct att tct gaa gaa gaa gaa atg gtc tat gaa cat gaa aag        2930
Asp Ile Ala Ile Ser Glu Glu Glu Glu Met Val Tyr Glu His Glu Lys
            880                 885                 890 tca aag ctt cat aaa aat ggt tat gaa cgc aaa tct tca act ggt caa        2978
Ser Lys Leu His Lys Asn Gly Tyr Glu Arg Lys Ser Ser Thr Gly Gln
        895                 900                 905 atc agt aga gaa tct agg aat gga aag att tgg aaa aac atc agg aaa        3026
Ile Ser Arg Glu Ser Arg Asn Gly Lys Ile Trp Lys Asn Ile Arg Lys
910                 915                 920                 925 act tgc tgc aag ata gta gag aac agc tgg ttt gag tgt ttc att ggc        3074
Thr Cys Cys Lys Ile Val Glu Asn Ser Trp Phe Glu Cys Phe Ile Gly
                930                 935                 940 ctg gtc act ctg ctc tgc aca ggc act ctg gct ctt gaa gac ata tat        3122
Leu Val Thr Leu Leu Cys Thr Gly Thr Leu Ala Leu Glu Asp Ile Tyr
            945                 950                 955 att gat cag aga aaa acc act aaa atc tta ctg gaa tat gcg gac atg        3170
Ile Asp Gln Arg Lys Thr Thr Lys Ile Leu Leu Glu Tyr Ala Asp Met
        960                 965                 970 ata ttt gca tac atc ttc att ctg gag atg ctt ctc aag tgg gtg gct        3218
Ile Phe Ala Tyr Ile Phe Ile Leu Glu Met Leu Leu Lys Trp Val Ala
975                 980                 985 tat ggc ttt aaa gcc ttt ttc tcc aac aac tgg tac aaa ctg gac ttt        3266
Tyr Gly Phe Lys Ala Phe Phe Ser Asn Asn Trp Tyr Lys Leu Asp Phe
990                 995                 1000                1005 atg gtt gtt atc gtg ttt tgt ctt agc tta ata ggc aaa act cga gaa        3314
Met Val Val Ile Val Phe Cys Leu Ser Leu Ile Gly Lys Thr Arg Glu
                1010                1015                1020 gat ctg aac cct ctg aca tca ata aag ttc ctt cga gca cta aga gtt        3362
Asp Leu Asn Pro Leu Thr Ser Ile Lys Phe Leu Arg Ala Leu Arg Val
            1025                1030                1035 ctg tcg cag ttt gaa aga atg aag gtg gtc ctg aga gct ttg ata aaa        3410
Leu Ser Gln Phe Glu Arg Met Lys Val Val Leu Arg Ala Leu Ile Lys
        1040                1045                1050 aca acc tta ccc act gtg agc gtg ttt cta gtc tgc cta atg atc tgg        3458
Thr Thr Leu Pro Thr Val Ser Val Phe Leu Val Cys Leu Met Ile Trp
    1055                1060                1065 ctg ctt ttc agt gtt att gga gtg cag tta ttt gct ggc aag ttc tat        3506
Leu Leu Phe Ser Val Ile Gly Val Gln Leu Phe Ala Gly Lys Phe Tyr
1070                1075                1080                1085 gaa tgc att gac cca aca aag gga gaa aga ttc cct gta ttt gaa gtt        3554
Glu Cys Ile Asp Pro Thr Lys Gly Glu Arg Phe Pro Val Phe Glu Val
                1090                1095                1100 atg aat aaa agt cag tgt gaa aaa ctg tta ttc aat gaa tca atg ccg        3602
Met Asn Lys Ser Gln Cys Glu Lys Leu Leu Phe Asn Glu Ser Met Pro
            1105                1110                1115 tgg gag aat gca aaa ctg aac ttt gat aat gtt gga aat ggt ttt ctt        3650
Trp Glu Asn Ala Lys Leu Asn Phe Asp Asn Val Gly Asn Gly Phe Leu
        1120                1125                1130 tct tta ctc caa gtg gca aca ttt aat gga tgg atc agt att atg aat        3698
Ser Leu Leu Gln Val Ala Thr Phe Asn Gly Trp Ile Ser Ile Met Asn
    1135                1140                1145 tca gca att gat tct gtt ggt gta aac atg cag ccc agc ttt gag tac        3746
Ser Ala Ile Asp Ser Val Gly Val Asn Met Gln Pro Ser Phe Glu Tyr
1150                1155                1160                1165
```

-continued

```
aac ctc tac atg tat agt tac ttt atc atc ttt gtt atc ttt gga tta         3794
Asn Leu Tyr Met Tyr Ser Tyr Phe Ile Ile Phe Val Ile Phe Gly Leu
            1170                1175                1180 ttt ctt cct ctc tgt atg ctg att ggt gtt att att cgc aat ttc aac         3842
Phe Leu Pro Leu Cys Met Leu Ile Gly Val Ile Ile Arg Asn Phe Asn
        1185                1190                1195 aag cag aaa att aag cag gga gga tca aac atc ttt ata aca gta aaa         3890
Lys Gln Lys Ile Lys Gln Gly Gly Ser Asn Ile Phe Ile Thr Val Lys
    1200                1205                1210 cag aaa aaa cag tac cgg gcc ctg aag aag ctc ttg tat gca gac gtc         3938
Gln Lys Lys Gln Tyr Arg Ala Leu Lys Lys Leu Leu Tyr Ala Asp Val
1215                1220                1225 cag aaa cca aca ccc cgc ccc aga aac aaa ttc caa ggc ttc ctt ttt         3986
Gln Lys Pro Thr Pro Arg Pro Arg Asn Lys Phe Gln Gly Phe Leu Phe
1230                1235                1240                1245 gac cta gta aca cac cgt gtc ttt aat gtt atc atc ata ctt ctt atc         4034
Asp Leu Val Thr His Arg Val Phe Asn Val Ile Ile Ile Leu Leu Ile
            1250                1255                1260 tgt ttc caa gca aca acc att atg ata caa aag gat gag cag agt cca         4082
Cys Phe Gln Ala Thr Thr Ile Met Ile Gln Lys Asp Glu Gln Ser Pro
        1265                1270                1275 caa atg gaa act gcc atc ttc tgg atg aac tcc att ttt gtc atg ctg         4130
Gln Met Glu Thr Ala Ile Phe Trp Met Asn Ser Ile Phe Val Met Leu
    1280                1285                1290 ttc act ctg gaa tgc ata ctg aag ctc act gcc ttc cgt tgc cac tac         4178
Phe Thr Leu Glu Cys Ile Leu Lys Leu Thr Ala Phe Arg Cys His Tyr
1295                1300                1305 ttc acc agt gca tgg aat gtt cat gac ttt atg gtg gtc att ttc tcc         4226
Phe Thr Ser Ala Trp Asn Val His Asp Phe Met Val Val Ile Phe Ser
1310                1315                1320                1325 att aca ggg ctg ctg cta ccc ttg aca ata gga caa tac ttt gtg cct         4274
Ile Thr Gly Leu Leu Leu Pro Leu Thr Ile Gly Gln Tyr Phe Val Pro
            1330                1335                1340 cct tcc ctg gtg cag ctg att ctt ctc tct cga gtc atc cac atc ctg         4322
Pro Ser Leu Val Gln Leu Ile Leu Leu Ser Arg Val Ile His Ile Leu
        1345                1350                1355 cgt cct ggg aaa gga ccg aag gtg ttc cat gac ctg atg ctt ccc ttg         4370
Arg Pro Gly Lys Gly Pro Lys Val Phe His Asp Leu Met Leu Pro Leu
    1360                1365                1370 att ctg gcg ctc cca gca ttg ctg aac att agt ctt ctc atc ttc ctg         4418
Ile Leu Ala Leu Pro Ala Leu Leu Asn Ile Ser Leu Leu Ile Phe Leu
1375                1380                1385 gtc atg ttc atc tac gcc atc ttt gga atg tac aac ttt gcc tat gta         4466
Val Met Phe Ile Tyr Ala Ile Phe Gly Met Tyr Asn Phe Ala Tyr Val
1390                1395                1400                1405 aag aaa gaa gcc gga att aat gat gtg tcc aac ttt gag acc ttt gga         4514
Lys Lys Glu Ala Gly Ile Asn Asp Val Ser Asn Phe Glu Thr Phe Gly
            1410                1415                1420 agc agt atg ctc tgt ctc ttc caa gtt aca acg ttt tct ggt tgg gac         4562
Ser Ser Met Leu Cys Leu Phe Gln Val Thr Thr Phe Ser Gly Trp Asp
        1425                1430                1435 ggg atg ctg gat gca att ttc aac agt cag tgg tct gac tgc gat cct         4610
Gly Met Leu Asp Ala Ile Phe Asn Ser Gln Trp Ser Asp Cys Asp Pro
    1440                1445                1450 gat aaa att aat cca ggg act cag gtc aag gga gat tgt ggg agc cct         4658
Asp Lys Ile Asn Pro Gly Thr Gln Val Lys Gly Asp Cys Gly Ser Pro
1455                1460                1465 tct gtt ggg att tct tat ttt gtc agt tac atc ctc ata tca tgg ttg         4706
Ser Val Gly Ile Ser Tyr Phe Val Ser Tyr Ile Leu Ile Ser Trp Leu
1470                1475                1480                1485
```

```
atc att gtt aac atg tac att gtg ttg atc atg gag ttc tta agt att       4754
Ile Ile Val Asn Met Tyr Ile Val Leu Ile Met Glu Phe Leu Ser Ile
        1490                1495                1500 cct tct cag aaa aaa agc agg acc ttg agt gaa gat gac ttt agg aga       4802
Pro Ser Gln Lys Lys Ser Arg Thr Leu Ser Glu Asp Asp Phe Arg Arg
        1505                1510                1515 ttc ttc cgg gtg tgg aac agg ttt gac cct gat agg acc cag tac ata       4850
Phe Phe Arg Val Trp Asn Arg Phe Asp Pro Asp Arg Thr Gln Tyr Ile
        1520                1525                1530 gac tct agc aag ctt tct gat ttt gca gct gct ctg gat cct cct ctt       4898
Asp Ser Ser Lys Leu Ser Asp Phe Ala Ala Ala Leu Asp Pro Pro Leu
    1535                1540                1545 ttc atg gca aaa cca aac aag ggc cag ctt gtg gcc atg gat ctc ccc       4946
Phe Met Ala Lys Pro Asn Lys Gly Gln Leu Val Ala Met Asp Leu Pro
1550                1555                1560                1565 atg gct gcg gga gac aga atc cac tgc ctc gac att tta ctt gcc ttt       4994
Met Ala Ala Gly Asp Arg Ile His Cys Leu Asp Ile Leu Leu Ala Phe
        1570                1575                1580 acg aaa aga gtg atg gga aag gat gag agg gtg gag aaa atc ctt tca       5042
Thr Lys Arg Val Met Gly Lys Asp Glu Arg Val Glu Lys Ile Leu Ser
        1585                1590                1595 gag ata gaa tcc ggg ttc atg tta gcg aac cct ttc aaa atc act tat       5090
Glu Ile Glu Ser Gly Phe Met Leu Ala Asn Pro Phe Lys Ile Thr Tyr
        1600                1605                1610 gag ccg att aca act act ttg aaa cgc aaa caa gag gca gtt tca gca       5138
Glu Pro Ile Thr Thr Thr Leu Lys Arg Lys Gln Glu Ala Val Ser Ala
    1615                1620                1625 acc atc atc cag cgt gca tat aaa agc tac cgc tta agg caa aat gac       5186
Thr Ile Ile Gln Arg Ala Tyr Lys Ser Tyr Arg Leu Arg Gln Asn Asp
1630                1635                1640                1645 aag aat gta tca gat act cct gct ata gat gac cgc aga gat gat ctt       5234
Lys Asn Val Ser Asp Thr Pro Ala Ile Asp Asp Arg Arg Asp Asp Leu
        1650                1655                1660 act tct aaa ggt gct cac tct ggc aaa atc gag gag aag gca tct att       5282
Thr Ser Lys Gly Ala His Ser Gly Lys Ile Glu Glu Lys Ala Ser Ile
        1665                1670                1675 cag acc cag att taa tgacacttcc cacttctact ttctttacat atgtccccaa       5337
Gln Thr Gln Ile
        1680 gcactaaatg ttaactgatc ttaagctgga gatcagaaac tagagataat gataacatct      5397 gtgtgcccag acatctccat gacaagctca gctttagggt cagtcttctg atgcatcaga      5457 aagacagcag ctcagcgttg ctgcg                                            5482

<210> SEQ ID NO 3
<211> LENGTH: 1681
<212> TYPE: PRT
<213> ORGANISM: Mus musculus

<400> SEQUENCE: 3

Met Leu Thr Ser Pro Glu Pro Lys Gly Leu Val Pro Phe Thr Thr Glu
1               5                   10                  15

Ser Leu Glu Leu Ile Glu Asn His Ile Ala Lys Lys Cys Asn Glu Asp
            20                  25                  30

Pro Glu Glu Glu Glu Gly Leu Lys Pro Ser Arg Asn Leu Glu Ala Gly
        35                  40                  45

Lys Arg Leu Pro Ile Pro Tyr Gly Thr Leu Pro Arg Gly Thr Val Ser
    50                  55                  60
```

-continued

```
Glu Pro Leu Glu Asp Val Asp Pro Tyr Tyr Tyr Val Lys Arg Asn Thr
 65                  70                  75                  80

Phe Met Val Leu Asn Arg Ser Arg Val Ile Phe Arg Phe Asn Ala Val
                 85                  90                  95

Ser Ile Phe Cys Thr Leu Ser Pro Leu Asn Ser Leu Arg Arg Ala Ala
            100                 105                 110

Ile Lys Ala Leu Val His Pro Leu Phe Arg Leu Leu Ile Leu Ile Ser
        115                 120                 125

Val Leu Thr Asp Ser Ile Leu Met Cys Met Ser Asn Leu Pro Glu Trp
130                 135                 140

Ile Leu Ala Ile Glu Asn Thr Leu Leu Gly Ile Tyr Ala Phe Glu Ile
145                 150                 155                 160

Leu Val Lys Val Ile Ala Arg Gly Ile Trp Ala Gly Ser Phe Ser Phe
                165                 170                 175

Leu Gly Asp Leu Trp Asn Trp Leu Asp Phe Ser Val Thr Leu Phe Glu
            180                 185                 190

Leu Ile Thr Arg Phe Ser Pro Leu Ser Ser Phe Leu Met Leu Lys Thr
        195                 200                 205

Ile Arg Thr Phe Arg Ile Leu Lys Ile Ile Pro Leu Asn His Gly Leu
        210                 215                 220

Gln Ser Ile Val Met Thr Leu Ala Gln Cys Leu Lys Lys Leu Phe Gly
225                 230                 235                 240

Ala Ile Ala Leu Ala Leu Phe Phe Leu Ala Val Phe Ser Leu Leu Gly
                245                 250                 255

Met Gly Leu Phe Met Gly Asn Leu Lys His Lys Cys Leu Arg Trp Pro
            260                 265                 270

Glu Glu Asn Glu Asn Glu Thr Leu His Asn Arg Thr Gly Ser Leu Asn
        275                 280                 285

Tyr Ser Pro Glu Arg Ile Asn Phe Tyr Tyr Met Glu Gly Ala Lys Tyr
        290                 295                 300

Ala Leu Leu Cys Gly Asn Arg Thr Asp Ala Gly Gln Cys Pro Glu Gly
305                 310                 315                 320

Tyr Val Cys Val Lys Glu Gly Thr Asn Pro Asp Asn Gly Phe Thr Ser
                325                 330                 335

Phe Asp Asn Phe Gly Trp Ser Leu Leu Ala Met Phe Arg Leu Met Thr
            340                 345                 350

Gln Asp Tyr Pro Glu Leu Leu Tyr His Gln Ile Leu Tyr Ala Ser Gly
        355                 360                 365

Lys Val Tyr Met Ile Phe Phe Val Met Ile Ser Phe Trp Phe Ala Phe
        370                 375                 380

Tyr Leu Thr Ser Leu Phe Leu Gly Ile Leu Thr Met Thr Tyr Glu Lys
385                 390                 395                 400

Glu Lys Gln Arg Ala Cys Glu Glu Ser Gly Gly Leu Asp Pro Lys Cys
                405                 410                 415

Gln Gln Thr Val Lys Glu Leu Asp Glu Asn Asp Ala Ala Glu Met
            420                 425                 430

Glu Thr Thr Gln Ile Glu Met Lys Lys Arg Ser Pro Thr Ser Ile Asn
        435                 440                 445

Thr Thr Leu Asp Ile Leu Glu Asp Thr Thr Leu Gly His Arg Glu Glu
        450                 455                 460

Pro Glu Thr Ser Arg Lys Lys Cys Pro Ile Cys Trp His Lys Phe Ile
465                 470                 475                 480

Lys Thr Cys Phe Ile Trp Lys Cys Ser Pro Cys Trp Val Lys Leu Asn
```

-continued

```
                485                 490                 495
Glu Phe Ala Asp Arg Val Ile Thr His Pro Leu Ala Asp Leu Phe Leu
            500                 505                 510
Val Ile Cys Ile Val Leu Asn Ile Cys Phe Leu Ala Leu Glu His Phe
            515                 520                 525
Pro Met Ser Glu Glu Leu Arg Ser Leu Leu His Val Gly Asn Leu Val
            530                 535                 540
Phe Ile Gly Ile Tyr Thr Ile Glu Leu Ile Leu Lys Ile Ile Ala Met
545                 550                 555                 560
His Pro Tyr Gly Tyr Phe Gln Ile Ser Trp Asn Ile Phe Asp Ser Ile
            565                 570                 575
Leu Val Val Leu Glu Leu Thr Glu Ile Leu Leu Ala Asp Val Glu Gly
            580                 585                 590
Leu Ala Val Leu Ile Thr Val Pro Leu Ile Phe Ile Lys Leu Gly Lys
            595                 600                 605
Tyr Gly Pro Pro Phe Lys Ser Leu Met Arg Ile Leu Gly Ser Ser Leu
            610                 615                 620
Met Ala Leu Lys Asp Leu Val Leu Leu Leu Cys Ile Phe Val Tyr Phe
625                 630                 635                 640
Ser Ala Val Phe Gly Met Lys Leu Phe Gly Arg Ser Tyr Lys Asp Cys
            645                 650                 655
Val Cys His Ile Lys Glu Asp Cys Gln Pro Gln Arg Trp His Met Ser
            660                 665                 670
Asp Phe Leu His Ala Tyr Met Thr Val Phe Arg Ile Leu Cys Gly Glu
            675                 680                 685
Trp Ile Glu Thr Leu Trp Glu Cys Met Glu Val Ala Gly Gln Ala Trp
            690                 695                 700
Cys Ile Pro Phe Tyr Met Met Val Ile Leu Ile Gly Asn Leu Leu Ile
705                 710                 715                 720
Leu Tyr Leu Phe Val Thr Leu Val Ser Ser Phe Ser Tyr Tyr Asp Ala
            725                 730                 735
Thr Ser Glu Val Asn Lys Glu Ala Lys Asn Leu Gln Leu Ala Met Ala
            740                 745                 750
Arg Ile Lys Ser Gly Ile Asn Ser Met Leu Leu Lys Leu Met Cys Thr
            755                 760                 765
Glu Arg Ser Val Pro Thr Glu Ala Thr Asp Gln Ile Cys Asp Pro Ser
            770                 775                 780
Val Lys Glu Asn Ile Ser Gly His Thr Leu Ser Glu Leu Ser Asn Thr
785                 790                 795                 800
Gln Thr Phe Leu Arg Tyr Lys Asp Gln Ser Ser Ser Thr Glu Lys Thr
            805                 810                 815
Pro Val Thr Glu Ser Glu Ser Gln Ser Leu Ile Ala Ser Pro Ser Ala
            820                 825                 830
Ser Glu Thr Val Pro Ile Ala Ser Gly Glu Ser Asp Ile Glu Asn Leu
            835                 840                 845
Asp Asn Lys Glu Thr Arg Ser Lys Ser Gly Asn Gly Gly Ser Lys Glu
            850                 855                 860
Lys Met Lys Gln Ser Ser Ser Glu Cys Ser Thr Val Asp Ile Ala
865                 870                 875                 880
Ile Ser Glu Glu Glu Glu Met Val Tyr Glu His Glu Lys Ser Lys Leu
            885                 890                 895
His Lys Asn Gly Tyr Glu Arg Lys Ser Ser Thr Gly Gln Ile Ser Arg
            900                 905                 910
```

-continued

```
Glu Ser Arg Asn Gly Lys Ile Trp Lys Asn Ile Arg Lys Thr Cys Cys
            915                 920                 925
Lys Ile Val Glu Asn Ser Trp Phe Glu Cys Phe Ile Gly Leu Val Thr
        930                 935                 940
Leu Leu Cys Thr Gly Thr Leu Ala Leu Glu Asp Ile Tyr Ile Asp Gln
945                 950                 955                 960
Arg Lys Thr Thr Lys Ile Leu Leu Glu Tyr Ala Asp Met Ile Phe Ala
                965                 970                 975
Tyr Ile Phe Ile Leu Glu Met Leu Leu Lys Trp Val Ala Tyr Gly Phe
            980                 985                 990
Lys Ala Phe Phe Ser Asn Asn Trp Tyr Lys Leu Asp Phe Met Val Val
        995                 1000                1005
Ile Val Phe Cys Leu Ser Leu Ile Gly Lys Thr Arg Glu Asp Leu Asn
    1010                1015                1020
Pro Leu Thr Ser Ile Lys Phe Leu Arg Ala Leu Arg Val Leu Ser Gln
1025                1030                1035                1040
Phe Glu Arg Met Lys Val Val Leu Arg Ala Leu Ile Lys Thr Thr Leu
                1045                1050                1055
Pro Thr Val Ser Val Phe Leu Val Cys Leu Met Ile Trp Leu Leu Phe
            1060                1065                1070
Ser Val Ile Gly Val Gln Leu Phe Ala Gly Lys Phe Tyr Glu Cys Ile
        1075                1080                1085
Asp Pro Thr Lys Gly Glu Arg Phe Pro Val Phe Glu Val Met Asn Lys
    1090                1095                1100
Ser Gln Cys Glu Lys Leu Leu Phe Asn Glu Ser Met Pro Trp Glu Asn
1105                1110                1115                1120
Ala Lys Leu Asn Phe Asp Asn Val Gly Asn Gly Phe Leu Ser Leu Leu
                1125                1130                1135
Gln Val Ala Thr Phe Asn Gly Trp Ile Ser Ile Met Asn Ser Ala Ile
            1140                1145                1150
Asp Ser Val Gly Val Asn Met Gln Pro Ser Phe Glu Tyr Asn Leu Tyr
        1155                1160                1165
Met Tyr Ser Tyr Phe Ile Ile Phe Val Ile Phe Gly Leu Phe Leu Pro
    1170                1175                1180
Leu Cys Met Leu Ile Gly Val Ile Ile Arg Asn Phe Asn Lys Gln Lys
1185                1190                1195                1200
Ile Lys Gln Gly Gly Ser Asn Ile Phe Ile Thr Val Lys Gln Lys Lys
                1205                1210                1215
Gln Tyr Arg Ala Leu Lys Lys Leu Leu Tyr Ala Asp Val Gln Lys Pro
            1220                1225                1230
Thr Pro Arg Pro Arg Asn Lys Phe Gln Gly Phe Leu Phe Asp Leu Val
        1235                1240                1245
Thr His Arg Val Phe Asn Val Ile Ile Leu Leu Ile Cys Phe Gln
    1250                1255                1260
Ala Thr Thr Ile Met Ile Gln Lys Asp Glu Gln Ser Pro Gln Met Glu
1265                1270                1275                1280
Thr Ala Ile Phe Trp Met Asn Ser Ile Phe Val Met Leu Phe Thr Leu
                1285                1290                1295
Glu Cys Ile Leu Lys Leu Thr Ala Phe Arg Cys His Tyr Phe Thr Ser
            1300                1305                1310
Ala Trp Asn Val His Asp Phe Met Val Val Ile Phe Ser Ile Thr Gly
        1315                1320                1325
```

Leu Leu Leu Pro Leu Thr Ile Gly Gln Tyr Phe Val Pro Pro Ser Leu
    1330                1335                1340

Val Gln Leu Ile Leu Leu Ser Arg Val Ile His Ile Leu Arg Pro Gly
1345                1350                1355                1360

Lys Gly Pro Lys Val Phe His Asp Leu Met Leu Pro Leu Ile Leu Ala
            1365                1370                1375

Leu Pro Ala Leu Leu Asn Ile Ser Leu Leu Ile Phe Leu Val Met Phe
        1380                1385                1390

Ile Tyr Ala Ile Phe Gly Met Tyr Asn Phe Ala Tyr Val Lys Lys Glu
    1395                1400                1405

Ala Gly Ile Asn Asp Val Ser Asn Phe Glu Thr Phe Gly Ser Ser Met
1410                1415                1420

Leu Cys Leu Phe Gln Val Thr Thr Phe Ser Gly Trp Asp Gly Met Leu
1425                1430                1435                1440

Asp Ala Ile Phe Asn Ser Gln Trp Ser Asp Cys Asp Pro Asp Lys Ile
            1445                1450                1455

Asn Pro Gly Thr Gln Val Lys Gly Asp Cys Gly Ser Pro Ser Val Gly
        1460                1465                1470

Ile Ser Tyr Phe Val Ser Tyr Ile Leu Ile Ser Trp Leu Ile Ile Val
    1475                1480                1485

Asn Met Tyr Ile Val Leu Ile Met Glu Phe Leu Ser Ile Pro Ser Gln
    1490                1495                1500

Lys Lys Ser Arg Thr Leu Ser Glu Asp Asp Phe Arg Arg Phe Phe Arg
1505                1510                1515                1520

Val Trp Asn Arg Phe Asp Pro Asp Arg Thr Gln Tyr Ile Asp Ser Ser
            1525                1530                1535

Lys Leu Ser Asp Phe Ala Ala Ala Leu Asp Pro Pro Leu Phe Met Ala
        1540                1545                1550

Lys Pro Asn Lys Gly Gln Leu Val Ala Met Asp Leu Pro Met Ala Ala
    1555                1560                1565

Gly Asp Arg Ile His Cys Leu Asp Ile Leu Leu Ala Phe Thr Lys Arg
    1570                1575                1580

Val Met Gly Lys Asp Glu Arg Val Glu Lys Ile Leu Ser Glu Ile Glu
1585                1590                1595                1600

Ser Gly Phe Met Leu Ala Asn Pro Phe Lys Ile Thr Tyr Glu Pro Ile
            1605                1610                1615

Thr Thr Thr Leu Lys Arg Lys Gln Glu Ala Val Ser Ala Thr Ile Ile
        1620                1625                1630

Gln Arg Ala Tyr Lys Ser Tyr Arg Leu Arg Gln Asn Asp Lys Asn Val
    1635                1640                1645

Ser Asp Thr Pro Ala Ile Asp Asp Arg Arg Asp Asp Leu Thr Ser Lys
    1650                1655                1660

Gly Ala His Ser Gly Lys Ile Glu Glu Lys Ala Ser Ile Gln Thr Gln
1665                1670                1675                1680

Ile

<210> SEQ ID NO 4
<211> LENGTH: 6927
<212> TYPE: DNA
<213> ORGANISM: Mus musculus

<400> SEQUENCE: 4
aagctttact ctcacagaga aaagtcttct gagtgatcaa ttgccaacga tacaacctca    60
ccttagttta ccctgacctg tgaaagatgg ccttcaacag tggagaataa ggagttctag   120

-continued

```
ctgagatgtt tcattaagcg acatattcat ggatcagctt ttgatggcag attttcaggc      180
tccttttctc cactgccaat aattttacaa aacacaattt taaaattgta gtctttatgg      240
gaaacaattc atcctataga tgttgtcaag gacaaaacat tttcactcct gggcagtttt      300
gttgttccct tccctcactg tcatggcgct aaagcggtag ctcatcccca gattaggggc      360
ccaggtgtaa ttgttcttaa gtctgaaatt gtaggggaga gttctttgaa ctcatctctt      420
catgagttca aagaacatat gacaacttat tgatagaatg actttacaca tggccatatt      480
ttacacattt actattttac aggtataaaa ccgaaaatgt tgacttcccc agagccgaag      540
ggccttgtcc catttacaac agagtcactt gaacttatag aaaatcacat tgctaaaaaa      600
tgcaatgaag accccgaaga agaagaaggt taaaaccaa gtcgtaatct agaagctggc       660
aaaagacttc caattcccta tggaaccctc cctcgaggaa ccgtgtcaga gcccttggaa      720
gatgtggatc catactacta tgttaagaga aatgtaagta ttaactgtta tcattgaagc      780
tatattttac ttcgcttata ttcagccact tgaaatgtaa ttgagataag acttaaagaa      840
aattaataga gaaggcattc tttcataatc tattctttgt gggggtcaac atgctcaaga      900
tagttaaacc tgataaaata tctgagtaat atattatggt taatgaccgt agtatatata      960
ctgctattcc ttaatataag tggctattgt gaaaatatgc taattaccat tttctgatta     1020
gcaattttaa aacaatcatg aaatatttag aatatggaca gaaatttcaa ataccttgat     1080
aacttactag tcaaaacagt acatttattt ttaatcatat ataaatccac aaattcaaac     1140
ctccctcatt tccaggaaga ctttagagac ctagaaatta tgtatacaca aacacacaca     1200
cacacataca cacacacaca cgcacacgca aatgcacacc ctaccatcac aaacacaaaa     1260
taagtacaag aatgatttct gttagaaaat tcagacatgt ggattgatga agatagatga     1320
gtcttgtttc aaaagcatgg tttgggggct ggagaaatgt ctcagtttct aatagcactg     1380
gctgttcttc tggacgtcat aagattgatt gcagtccctg tacagtaggt cacagccttt     1440
tgtaactcta gttccagaag atttgacctt ctttttggcca ctatgggcac tgggaatgca     1500
aataattcat atatgcacac agtgaagaca tctatatact tgaaatgaga taaaatttta     1560
ggtacagctt gcagaatact tggaatttta ataaagccaa ggtagaacag tttaaggaca     1620
aatggaatgg caacagccaa gattgattct acaagagggc atagaaaggg ctgtgctatt     1680
actggaaaat cagttatgtt gttgactgtg gcaaacatga gagagtggag gtgtcatcat     1740
ggaattactg tagtggacaa ggtcatttgg ggtgaatgtg gcagatgaat aaaaccaagc     1800 taatacctt cttaattaaa agaaagtga tcaatacaga aaataaaata gaacataaaa      1860
gacagggaga aatataaggt agagaagagg aggagagaaa gagatgaggg agaagagaag     1920
gggtgagaat gggaagagga agagaagaga gataggtaga aatgaagaga ggggaggaag     1980
ggacttgtat attacagtta atttacctag tgtacaaact gatagttctt agtataaatg     2040
gcttttatgt aaatatgatg attactgtct tctaattatc tattttttaaa taatcataaa     2100 atatttacac tataaagaa aaagagagaa ggagggagaga aagaacaaga aggaaatagg     2160
gtagagggaa ccctgagatt cagtgtctat gtcaggaaaa gaaacagtaa aatatgactg     2220
atgaaaaatg ccaatgtctg tagcttgaaa gagtgaagtt acattgacag aaagtgaaat     2280
aaagtttatt tactagcatc ttgatattca tgtatcatat tcactgatgt tatatctaat     2340
gaggagatga gactgaacga aaatatctgc agaaaaatac attcattgca taactgttcc     2400
tataataatg tcatggtgtc atttgaaata ttttaaggac attttagtta aaatgcaagt     2460
```

```
tcagtcctca tttgtattgt tctggcactc actttgtggt gtgcttgagt tgataatggc    2520
cagtaacctt aggattgcct gtcaatattg cagccatctt aatactgagt aaggtatgca    2580
ggcatgctag acatgggaat actgccattg aagataaaat caaagctctt aagaaacaaa    2640
acaaatactt tatgacaggc cccatgtcca gcagtagttg gccaaaaaaa aaaaaaaaaa    2700
ttgtgatttt gattcttttg tcaggtggc atgtttggag acagggattc cctgagtagc     2760
cctggctgtc ctggaactca ctctgcagtc caggctggcc tcgaactcag agatctgctt    2820
gcttctgtct tctgagttct aggattacgg gtataagttt ttattaaaag tataaggctt    2880 tgcttttttgt tgttgttttt ttttgtttgt ttgtttgttt tgtttttttgg ttggttgttt   2940 ttgttgttgt tggtggtggt ggtggtagtg gtgtgtgtgt gtgtgtgtgt gtgtgtgtgt    3000
gtgtgtgtgt gtgtgtgtgt gtgtggaggg agagagagag tgtgctgttt ctgttggaat    3060
tttttgtcat ttttctttaa cttgttatgt tttggtttct ttgagaaaga atgaaggaac    3120
ctgaagttgg ttggatacgg gtgtggggag gatcttggaa tgagttgaga aaggacaaag    3180
aatataatca aagcttacta tatgaaaaat taaataaaat gtgaaataac tacaaaaatc    3240
tcaaaacaac attttgagtg atttaggatc ctagcagcta tgaggcccat gggttgaaat    3300
ttgccagtga cttcatgcac tctaaagcct gcaaatgtga cttcatgaac tctgaagcct    3360
gccagggtga cctcatgctc tttgaagcct gactgggtga ctttatgcac tcagtgctgc    3420
tctcagtaac atcacactgt tcaagtatct gggttgtatt tggcttactc tcttacacat    3480
agcacagaga caaataatca taaaattaag actatgtatg aaatcaggag aaaacctgaa    3540
agtacgcatc ccttcacaat gacacacaca tatattgaac tccacatgga gtctgcaatt    3600
gttttggaag ctactatgga aagtagaatt tacacaacca ggtatattat ttgtttctac    3660
ctgttttatt taagtggaga tgggagaata ggtacaatag ttaaacaaag cctcatagca    3720
gttatatatt gaactacact tatctgagaa ttgagaccca gagtagattc cagttagagc    3780
agacatgcat ggagaagtgt tggcagttgt atattcttat aatttctttt tcatatgcgt    3840
ctgtcaacat aggaagcaat aagtcatacc tcctatatca ttatcagaat atatggtaga    3900
ctgtatagtc tattctattg catataagat taattttttaa gccaggcctt ctggcagggc    3960
tataattctc aaacaacaaa gtattgcaga ttcaagtcct ctgtggtcta aactgtgagt    4020
tcaaggtcag ccttaacaat ttaatgaaat ctatttttcaa gagaaaaaga atataaagat   4080
cctcaggaga aataatggaa gagagtttgc ccagcacaca tgaggcccct gtcacagagg    4140
aagaaaatat tacatatttt ttatttataa aaatatagtt atcttattat ataacatgct    4200
atgttatgtt atgttttatg ttataacaca tgacatttaa tctcatagtt ttcagaatta    4260
actggatttt cagtgttagc tggatcaaac tcagggcctg ctgaagggtg aacaaacact    4320
gttcttcaag ttacattacc agacagtaca tgttaatgca cccctacatt aatactttct    4380
ctgaagggac atatatagta aacacacaca cacacacaca cacacatata tatatatata    4440
catatacaca cacacatata tatatacact ttcaattacc atatataata tataccatat    4500
acattatagt aatgttcatt tatatgaaca aatgtaaaaa tgagcacaca tatgtatgaa    4560
tgtacataag cccacatgta catatgtata aataagccca tccacctacc tatatattga    4620
acaatgtctg ttttagaata tttatgtttc ttactatatt tattaagact tagtactttta   4680 gtatccacaa tccttgtgtt tatattacat aaattactat ttttagatag gttcatatca    4740
ataatattaa ataagttagg ttttgtaaaa acattaattt ttaggattta ccttgtaatt    4800
gttttatttt tttattcgat atttttcttta tttacatttc aaatgctttc ccgaaagtcc    4860
```

-continued

```
cctatacccct cccacctccc tgctccccta ctcacccact cccatttctt ggccctggtg    4920
ttcccctgta ttgggcata taaagtttgc aagaccaagg ggtctctatt cccaatgatg     4980
gccgactagg ccatcttctg ctacatattc agctagagac acgagctctg gggatactgg    5040
ttaataattg ttttattttt aatatatttt atttaaaata gaattacata aattatcctc    5100
ttattttctc ccctacagtg tctccctcat aaataatata aacaattgat gtgagatttg    5160
accattgctt ttataacact tcattgactt tttttctgat ataaaattaa aatttttaca    5220
ttcattaagt tatgagataa aggccctctg atgctttgaa tgcaaatcca cacaccatct    5280
gaagagtttc tttttcatta gttcaaggtg tgattgcacc ataatgactt tcttaagtac    5340
aaaccagcaa aaaataaata aattaattaa ttattaaaat aaaataagtg gtgagctatc    5400
aggcaagtcc aaatataagt gaaaactact ccctttgctt taaaaacaaa tgtcaaagcc    5460
aatgaaaata tgaaataatt tcaaactggt gagcattggt aatatgttgc ttcagttctc    5520
cattctgttt gttaatgtct ttcctgtggt tccttacaga ctttcatggt cttaaacaga    5580
agcagagtca tcttcaggtt caatgcggtt tccatcttct gcacattgtc tcctctaaac    5640
tccctcagaa gagcagctat caaggctttg gtgcatccat atccttcaa agtgtgatgg     5700 gttgtgtcat cggcatacta aaaataagtc ctgatgttct gtcattcaac ccctgttgta    5760
gtaatattta acaaatatca attcttattc ttcaaataga atgacatgta ttttcaatat    5820
ttacaaaaga atctcgcccc ttatatctac agatgcaatt tactggtctt ttgtaatgtg    5880
atttcttctc cattattcct tgaccctggc ttacccttt tcgcctgctg attttaatca     5940
gcgttctcac tgacagcata cttatgtgca tgagtaatct accagaatgg atattggcaa    6000
tagagtaagt tacttagttt tgctatatat aataaagtct gtaattatat tttggtttta    6060 acatttaat attattgta ttccattaaa ttacaaaaac atgttatgaa atgaaacatg      6120
atactattta aattttaaa tgtttaaaaa agttataaag acaagaggtt tgtttcactc     6180
acagctttga aggttcaaga gcacctatgc tgttcagctt cagggacaat taggtcctct    6240
cacctaatta acctgtggcc tgtggaaaca ggagaagctc tttcagaagc agccattcat    6300
gtcttgatgc tgtaagccca tgactggtat gaagcctgcc acaacttttc tcttactctt    6360
cttgtgggtc ttgtgcaaac aagcaggcat gcgctccagt gccacaagga ccttcaagtg    6420 cacccccacgt ctagtgctcc gtaaactctt gcctcaccat gatcgggatc aagttctaaa   6480
tatgtagaat attgtagaca tctgaaaaca aacctcatct tcatatttct tttctgtata    6540
tactcgtatg tttgtggggc atagcaatat gaacaccatg actaaatttt ctaaataaaa    6600
caaacatgta tatgcacata cacatatata tagatgtata ttcatcaatt tggggtttta    6660
ttttgccctt tcattcttct tacttaattc ctgttggtgt tatttatttt gattcatgtt    6720
ctttatacca cttgcctttg actcctgttc cagactcttg aatcctggaa ttacatcttc    6780
ttatcacgac tttacatatc tacagttcta tatagactga aggtttaatt atattaatta    6840
attatgttca ttggaatatt taggtccttt gctaaatgta tataccatgt ttcacctcat    6900
gcttgttttc ttccttattt aaagctt                                        6927
```

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence:Primer1

-continued

```
<400> SEQUENCE: 5
atgttgactt ccccagagcc                                                    20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence:Primer2

<400> SEQUENCE: 6
aaccaggcaa agcgccattc                                                    20

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence:Primer3

<400> SEQUENCE: 7
catcttccaa gggctctgac a                                                  21

<210> SEQ ID NO 8
<211> LENGTH: 16
<212> TYPE: PRT
<213> ORGANISM: Rattus norvegicus

<400> SEQUENCE: 8

Ser Val Ser Glu Thr Val Pro Ile Ala Ser Gly Glu Ser Asp Ile Lys
 1               5                  10                  15
```